(12) United States Patent
Bukshpan

(10) Patent No.: US 7,459,021 B2
(45) Date of Patent: Dec. 2, 2008

(54) METHODS AND APPARATUS FOR RAPID CRYSTALLIZATION OF BIOMOLECULES

(76) Inventor: Shmuel Bukshpan, 11/8 Hagana Street, Ramat Hasharon (IL) 47203

( * ) Notice: Subject to any disclaimer, the term of this patent is extended or adjusted under 35 U.S.C. 154(b) by 231 days.

(21) Appl. No.: 10/561,244

(22) PCT Filed: Sep. 2, 2004

(86) PCT No.: PCT/IL2004/000794

§ 371 (c)(1),
(2), (4) Date: Dec. 19, 2005

(87) PCT Pub. No.: WO2005/021841

PCT Pub. Date: Mar. 10, 2005

(65) Prior Publication Data

US 2006/0137603 A1    Jun. 29, 2006

Related U.S. Application Data

(60) Provisional application No. 60/499,360, filed on Sep. 3, 2003, provisional application No. 60/533,245, filed on Dec. 31, 2003.

(51) Int. Cl.
*C30B 7/00* (2006.01)
(52) U.S. Cl. .............................. 117/68; 117/69; 117/70; 422/245.1
(58) Field of Classification Search .................. 117/68, 117/69, 70; 422/245.1
See application file for complete search history.

(56) References Cited

U.S. PATENT DOCUMENTS

| | | | |
|---|---|---|---|
| 3,485,736 A | 12/1969 | Vesterberg | 204/548 |
| 4,130,470 A | 12/1978 | Rosengren et al. | 204/451 |
| 4,169,036 A | 9/1979 | Anderson et al. | 425/543 |
| 4,243,507 A | 1/1981 | Martin et al. | |
| 4,330,363 A | 5/1982 | Biegesen et al. | |
| 4,495,279 A | 1/1985 | Karpetsky et al. | |
| 4,594,064 A | 6/1986 | Anderson | 425/145 |
| 4,737,232 A | 4/1988 | Flicstein et al. | |
| 4,971,670 A | 11/1990 | Faupel et al. | |
| 5,082,548 A | 1/1992 | Faupel et al. | |
| 5,104,478 A | 4/1992 | Sikdar et al. | |
| 5,164,065 A | 11/1992 | Bettencourt et al. | 204/619 |
| 5,185,243 A | 2/1993 | Ullman et al. | 435/6 |

(Continued)

FOREIGN PATENT DOCUMENTS

EP    265214 A2    4/1988

(Continued)

OTHER PUBLICATIONS

Sauter et al, "Towards atomic resolution with crystals grown in gel: the case of thaumatin seen at room temperature," Proteins 48(2):146-150 (2002).

(Continued)

*Primary Examiner*—Robert M Kunemund
(74) *Attorney, Agent, or Firm*—Winston & Strawn LLP

(57) ABSTRACT

The present invention relates to methods and apparatus for promoting rapid formation of biomolecule crystals from a solution of biomolecules, preferably proteins, wherein the protein solution undergoes rapid concentration according to its isoelectric point in an electric field. Protein crystallization according to the methods of the present invention takes place within a period of hours or less.

55 Claims, 15 Drawing Sheets

U.S. PATENT DOCUMENTS

| | | | |
|---|---|---|---|
| 5,271,795 | A | 12/1993 | Ataka et al. |
| 5,304,292 | A | 4/1994 | Jacobs et al. ............... 204/619 |
| 5,447,612 | A | 9/1995 | Bier et al. |
| 5,451,662 | A | 9/1995 | Naveh et al. |
| 5,464,517 | A | 11/1995 | Hjerten et al. |
| 5,480,562 | A | 1/1996 | Lemelson |
| 5,525,198 | A * | 6/1996 | Craig et al. ............... 204/165 |
| 5,597,457 | A | 1/1997 | Craig et al. |
| 5,728,559 | A | 3/1998 | Nilsson et al. |
| 5,976,325 | A | 11/1999 | Blanks |
| 6,174,365 | B1 * | 1/2001 | Sanjoh ...................... 117/68 |
| 6,268,158 | B1 | 7/2001 | Pantoliano et al. |
| 6,344,326 | B1 | 2/2002 | Nelson et al. |
| 6,409,832 | B2 | 6/2002 | Weigl et al. |
| 6,500,933 | B1 | 12/2002 | Margolin et al. |
| 6,537,432 | B1 | 3/2003 | Schneider et al. |
| 6,541,606 | B2 | 4/2003 | Margolin et al. |
| 6,554,991 | B1 | 4/2003 | Goodman et al. .......... 204/613 |
| 6,579,358 | B2 | 6/2003 | Delucas |
| 6,593,118 | B2 | 7/2003 | Heng |
| 6,596,077 | B2 | 7/2003 | Meyerson |
| 6,602,391 | B2 | 8/2003 | Serikov |
| 6,808,934 | B2 | 10/2004 | Mutz et al. |
| 2003/0102215 | A1 | 6/2003 | Bukshpan et al. |
| 2004/0033166 | A1 * | 2/2004 | Arnowitz et al. ......... 422/82.05 |

FOREIGN PATENT DOCUMENTS

| | | |
|---|---|---|
| EP | 0302175 | 2/1989 |
| WO | WO 96/40049 | 12/1996 |
| WO | WO 97/04801 | 2/1997 |
| WO | WO 03/008977 | 1/2003 |
| WO | 2005054548 A2 | 6/2005 |

OTHER PUBLICATIONS

J. Sambrook, et al., Electrophoresis Buffers, Molecular Cloning, A Laboratory Manual, Second Edition, Cold Spring Harbor Laboratory Press, NY, pp. B.23- B.24, (1989).
Bernstein et al., J. Mol. Biol., 112, pp. 535-542 (1977).
C. W. Carter, Jr. and C. W. Carter, J. Biol. Chem., 254, pp. 12219-12223 (1979).
Scopes, Protein Purification: Principles and Practice, Springer-Verlag, NY, (1982).
Righetti, P. G., Isoelectric Focusing: Theory, Methodology and Applications, Eds., Work and Burdon, Elsevier Science Publishers B. V., Amsterdam, pp. 31-50 (1983).
Bjellquist et al., J. Biochem. Biophys. Methods, 6, pp. 317 (1983).
Allen, RC et al., Gel Electrophoresis and Isoelectric Focusing of Proteins: Selectd Techniques, Berlin: Walter de Gruyter & Co. (1984).
Altland et al., "Pouring reproducible gradients in gels under computer control: new devices for simultaneous delivery of two independent gradients, for more flexible slope and pH range of immobilized pH gradients". Clin Chem. Dec. 1984;30 (12 Pt 1):2098-103.
Matthews, et al., Anal. Biochem., 151, pp. 205-209 (1985).
McPherson, Methods Enzymol., 114, pp. 112-120 (1985).
Gilliland, J. Crystal Growth, 90, pp. 51-59 (1988).
Deutscher, Meth. Enzymology, 182, pp. 83-89 (1990).
Zewert and Harrington, Electrophoresis 13, pp. 824-831 (1992).
Henderson et al., Advances in Immunology, 62, pp. 217-256 (1996).
Sauter et al., Proteins: Structure, Function, and Genetics 48: 146-150 (2002).

* cited by examiner

ELECTRIC FIELD →

A

B

A

B

A

B

METHODS AND APPARATUS FOR RAPID CRYSTALLIZATION OF BIOMOLECULES

FIELD OF THE INVENTION

The present invention relates to methods and apparatus for promoting rapid formation of biomolecule crystals from a solution of biomolecules, preferably proteins, wherein the protein solution undergoes rapid concentration according to its isoelectric point in an electric field. Protein crystallization according to the methods of the present invention takes place within a period of hours or less.

BACKGROUND OF THE INVENTION

Protein crystallization has three major applications: (1) structural biology and drug design, (2) bioseparations, and (3) purification. Crystal formation is a slow, and tedious process typically based on preparation of a saturated protein solution following nucleation, at optimal conditions. Optimal conditions for protein crystallization include optimal protein concentration in the saturated solution, pH and temperature among others whereas these conditions are determined by extensive trial and error experiments.

Conventional protein crystallization methods and methods for determining the conditions that facilitate protein crystallization are disclosed in U.S. Pat. Nos. 6,596,077; 6,593,118; 6,579,358; 6,500,933; 6,409,832; 6,268,158; 5,976,325; 5,728,559; 5,271,795; 5,104,478; 4,737,232 and 4,330,363 among others.

Crystallization of bio-molecules, specifically proteins, in gels such as Silica hydrogel, agarose and polyacrylamide, is known in the art (e.g. CrystalEx™, Hampton Research Corp.). This method is considered advantageous since it is devoid of considerations of buoyancy, convection and sedimentation as compared with growth from liquid solutions. This method further regulates molecular diffusion, by the viscosity of the gel, and hence mimics in many respects the beneficial properties of crystal growth in microgravity environment like space. Another advantage of this method is that the crystals are maintained encapsulated in the gel at ambient temperature and in that configuration can even be directly subjected to the X-ray diffraction. This method basically involves adding a protein solution at concentrations of 10-20 mg/ml to a gel either prior to polymerization or following polymerization following storage within the gel at a controlled temperature for days to weeks, until protein crystallization takes place. It was shown that using this method, appropriate crystals were obtained (Sauter et al., Proteins: Structure, Function and Genetics 48:146-150, 2002), however, this method is rarely employed for protein crystal growth and is as slow as the other methods known in the art.

Isoelectric focusing (IEF) technique is widely used for protein separation and purification on the basis of their characteristic net electrical charge that varies with pH. Proteins are subjected to an electric field in a pH gradient wherein each protein migrates to a point within the gradient at which its net charge is zero, this point is called "the isoelectric point" or "pI".

IEF techniques for protein separation and purification are described in WO03/008977, by the inventor of the present invention, U.S. Pat. Nos. 6,537,432; 5,480,562; 5,464,517; 5,451,662; 5,082,548; 4,971,670; 4,495,279; and 4,243,507 among others.

There is an unmet need to overcome the obstacles encountered with crystal growth and to provide more rapid and less exhaustive means for enabling crystallization, particularly, protein crystallization.

SUMMARY OF THE INVENTION

The present invention relates to methods and apparatus for rapid crystallization of biomolecules, typically within no more than a few hours, using isoelectric focusing for obtaining a concentrated solution of the biomolecules followed by a fast crystallization of said biomolecules.

The present invention is based in part on the unexpected discovery that concentrating a dilute protein solution by utilizing any IEF procedure, generates a protein solution that facilitates rapid crystallization of the proteins within the solution.

According to one aspect, the present invention provides a method for rapid crystallization of biomolecules, comprising:
(a) providing at least one biomolecule species;
(b) providing at least one crystallization reactor comprising an IEF buffer having a pH range, the pH range encompassing the pI of the at least one biomolecule species;
(c) bringing said at least one biomolecule species into contact with the at least one crystallization reactor;
(d) introducing an electric field at said at least one crystallization reactor thereby generating a concentrated solution of said at least one biomolecule species; and
(e) obtaining at least one crystal within said at least one crystallization reactor.

According to another embodiment, step (c) further comprises depositing the at least one crystallization reactor and the at least one biomolecule species in running buffer. Preferably, step (c) further comprises stirring the running buffer. Advantageously, step (e) further comprises monitoring the formation of the biomolecule crystal.

According to yet another embodiment, the crystallization occurs within 24 hours, preferably within less than 12 hours.

According to alternative embodiments, the at least one biomolecule species is provided in a medium selected from the group consisting of: solution, gel and suspension.

According to another alternative embodiment, the at least one biomolecule species is immobilized onto a solid substrate.

The terms "crystallization reactor" or "reactor" as used herein refer to any medium of predetermined volume, density, and viscosity, comprising an IEF buffer having a pH range. According to some embodiments, the IEF buffer further comprises at least one polymer wherein the resulting crystallization reactor having a predetermined porosity. The density, viscosity, pore size (in cases where the IEF buffer comprises a polymer) and the volume of the crystallization reactor are designed such that desired biomolecules can enter the reactor, and can further diffuse therein. The volume of the crystallization reactor depends on the amount of desired biomolecules that is used. Within that volume crystallization takes place. Preferably, the crystallization reactor according to the present invention is functionally stable under the influence of an electric field.

As used herein, "IEF buffer" is used in its broadest meaning to signify a buffer comprising components, also termed hereinafter buffering agents, that have buffering capacities around a given pH value. Alternatively, the buffer may comprise components that organize to form a pH gradient, including, but not limited to, ampholytes, ampholines, acrylamide derivatives or a combination of buffering agents. The IEF buffer according to the present invention is typically a component of a crystallization reactor and is in the form of viscous liquid, slurry or gel. According to the present invention a biomolecule can pass through the IEF buffer unless the pI of the biomolecule falls within the pH range of the IEF buffer. Preferably, the IEF buffer according to the present invention is functionally stable under the influence of an electric field.

According to yet another embodiment, the at least one biomolecule species is selected from the group consisting of: protein complexes comprising chemical entities, peptides, proteins, polypeptides, enzymes, antibodies, protein-DNA complexes, polynucleotides, DNA, RNA, antigens, antigenic epitopes and variants thereof, hormones, carbohydrates, lipids, phospholipids and biotinylated probes. According to a preferred embodiment, the biomolecule is a protein. Preferably, the biomolecule is selected from a protein, a peptide or a polypeptide.

According to yet another embodiment, the at least one crystallization reactor is provided within a capillary. According to yet another embodiment, the at least one crystallization reactor is linked, joined, or substantially contiguous to a solid substrate.

According to yet another embodiment, the at least one crystallization reactor comprises a polymer, the polymer comprises one or more substances selected from the group consisting of: linear polymers, branched polymers, polyacrylamide, agarose, hydrogels, cellulose, modified cellulose, cross-linked polyvinyl alcohol, cross-linked polyethylene oxide and glycol polymer. According to yet another embodiment, the substrate used in step (b) comprises a polymer.

According to yet another embodiment, the at least one crystallization reactor further comprises a polymer, the polymer comprises at least one substance selected from the group consisting of: branched polymer, linear polymer, polyacrylamide, agarose, hydrogel, glycol polymer, cellulose, modified cellulose, cross-linked polyvinyl alcohol, cross-linked polyethylene oxide and glycol polymer.

According to yet another embodiment, the IEF buffer has a narrow pH range of no more than 0.2 pH units, preferably no more than 0.1 pH units, more preferably of no more than 0.02 pH units.

According to yet another embodiment, the temperature of the running solution is maintained within the range of 0-30° C.

According to yet another embodiment, the temperature of the running solution is maintained within the range of 0-30° C., and the electric field intensity is maintained between 50 V/cm to 2000 V/cm.

According to yet another embodiment, step (d) is occurs in the presence of a device capable of providing an electric field, the electric field being supplied as DC or AC.

According to certain embodiment, the device comprises a cathode electrode, an anode electrode and a voltage power supply. According to one embodiment, the electrodes are placed on opposite sides of the crystallization reactor such that the electrical field passes through or into the reactor. According to another embodiment, the electrodes are wires. According to yet another embodiment, the electrodes are parallel sets of wires or thin plates. According to yet another embodiment, the electrodes are made of or coated with a material selected from the group consisting of: platinum, titanium, chromium, gold, tantalum, palladium, palladium oxide, germanium, nickel and rhodium and alloys comprising same. Preferably, the electrodes are made of or coated with palladium, platinum, titanium, carbon or alloys comprising same.

The device functions to direct the biomolecules into the crystallization reactor. Thus, according to yet another embodiment, the electric field is selected from an alternating electric field or a direct electric field. If the crystallization reactor is contained within a closed system (e.g., the electrical field cannot pass through one side of the reactor and out the opposing side of the reactor), then it is advantageous that the device is capable of directing an electrical field in and out of the crystallization reactor comprising the buffer (i.e., an alternating electrical field).

According to other embodiment, the at least one crystallization reactor can have any desired shape and geometrical form.

According to yet another embodiment, the at least one crystallization reactor has a cylindrical form. According to some embodiments, the diameter of said at least one crystallization reactor is from about 20 μm to about 10 mm. According to some other embodiments, the length of said at least one crystallization reactor is from about 0.5 mm to about 10 mm.

According to various embodiments, step (a) of the method of the invention comprising: providing a plurality of crystallization reactors, each crystallization reactor comprises an IEF buffer, the IEF buffers in the plurality of crystallization reactors are similar or different from one another. According to a preferred embodiment, the crystallization reactors are isolated from one another. According to a certain embodiment, step (e) comprising: obtaining at least one crystal within each crystallization reactor. According to an alternative embodiment, step (e) comprising: obtaining a plurality of crystals within the plurality of crystallization reactors.

According to one embodiments, each IEF buffer has a narrow pH range of no more than 0.2 pH units, preferably no more than 0.1 pH units, more preferably of no more than 0.02 pH units. According to another embodiment, the pH ranges of the plurality of crystallization reactors do not overlap. Alternatively, the pH ranges of the plurality of crystallization reactors partially overlap. The term "partially overlap" as used herein is to be construed in its most general sense and refers, for example, to a plurality of pH ranges wherein the upper limit of one pH range overlaps with the lower limit of at least one other pH range. Alternatively, this term may refer to a plurality of pH ranges wherein one pH range is wider than at least one other pH range such that the wider pH range completely encompasses the one other pH range.

According to yet another embodiment, the pH step between one or more IEF buffers is no more than 0.1 pH units, preferably, no more than 0.02 pH units. The term "pH step" refers to the incremental difference in pH values between two different IEF buffers having different or partially different pH ranges. The pH step may refer to the difference between the upper limit of one pH range and the lower limit of another pH range. Alternatively, the pH step may refer to the difference between the central pH value of one pH range to the central pH value of another pH range.

According to yet another embodiment the plurality of crystallization reactors are linked, joined, or substantially contiguous to a substrate. According to an alternative embodiment, the crystallization reactors are linked, joined, or substantially contiguous with a substrate in a spatially addressable manner. According to yet another embodiment, the substrate is biomolecule impermeable. According to yet another embodiment, the substrate is ion impermeable.

According to yet another embodiment, a substrate comprising a plurality of crystallization reactors may be of an arrangement selected from the group consisting of: immobilized pH gradient, pH membranes and pre-cast gels.

According to another aspect the present invention provides a method for sorting a solution comprising a plurality of biomolecules and rapidly crystallizing at least one biomolecule species selected therefrom, the method comprising:

(a) providing a medium comprising a plurality of biomolecules;

(b) sorting the plurality of biomolecules on a substrate, thereby obtaining at least one locus on the substrate comprising at least one biomolecule species;

(c) recovering a portion from said substrate, the portion comprising the at least one locus;

(d) providing at least one crystallization reactor comprising an IEF buffer having a pH range, the pH range encompassing the pI of the at least one biomolecule species;

(e) bringing the portion of (c) into contact with the at least one crystallization reactor;

(f) introducing an electric field at the at least one crystallization reactor thereby generating within said at least one crystallization reactor a concentrated solution of said at least one biomolecule species; and (g) obtaining at least one biomolecule crystal within said at least one crystallization reactor.

According to an alternative embodiment, step (b) comprises: sorting the plurality of biomolecule on a substrate, thereby obtaining at least one locus on the substrate the locus comprising one biomolecule species.

According to one embodiment, sorting in step (b) is by the mass of the at least one biomolecule species. According to another embodiment, step (b) is carried out by a method selected from the group consisting of: isoelectric focusing, thin layer chromatography (TLC), including High Performance Liquid Chromatography (HPLC) techniques, and gel electrophoresis. Preferably, any one of the methods is performed under non-denaturing conditions.

According to yet another embodiment, wherein step (e) further comprising: depositing said portion and said at least one crystallization reactor in running buffer. Preferably, step (e) further comprising: stirring the running buffer. Advantageously, step (g) further comprises monitoring and/or detecting the formation of a biomolecule crystal.

According to yet another embodiment, crystals are obtained within 24 hours, preferably within 12 hours.

According to yet another embodiment, the IEF buffer of step (d) has a pH range of no more than 0.2 pH units, preferably no more than 0.1 pH units, more preferably of no more than 0.02 pH units.

According to yet another embodiment, the temperature of the running solution is maintained within the range of 0-30° C. According to yet another embodiment, the temperature of the running solution is maintained within the range of 0-30° C., and the electric field is maintained between 50 V/cm to 2000 V/cm. According to yet another embodiment, the electric field is being supplied as DC or AC.

According to yet another embodiment, the substrate used in step (b) is a gel. According to an alternative embodiment, the substrate used in step (b) comprises a polymer selected from the group consisting of: polyacrylamide, agarose, hydrogels, cellulose, nitrocellulose, modified cellulose, cross-linked polyvinyl alcohol, cross-linked polyethylene oxide and glycol polymer. According to yet another embodiment, the substrate used in step (b) comprises a polymer wherein step (f) comprising:

introducing an electric field to the at least one crystallization reactor thereby generating at said at least one crystallization reactor a concentrated band of said at least one biomolecule species;

According to yet another embodiment, the methods of the present invention are automated and are suitable for high-throughput crystallization of biomolecules, preferably proteins.

The method of the present invention is advantageous over methods known in the art for protein crystallization in that it promotes rapid protein crystallization, typically within less than one hour. In addition, the method of the present invention enables obtaining large crystals and is thus suitable for applications that require sufficiently large crystals, for example, collection of X-ray diffraction data of high quality.

Rapid crystallization in accordance with the methods of the present invention can be achieved using many of the IEF systems known in the art, such as, immobilized pH gradient (IPG) strips, pH membranes and any composition of ampholines in gel having the desired pH range, with the proviso that the IEF system meets, or is modified to meet, the principles of the present invention. Preferably, an IEF system according to the present invention comprises a plurality of distinct entities, also termed crystallization reactors, each crystallization reactor has an IEF buffer having a pH range. Optionally, the crystallization reactors are isolated from one another, thus establishing a system of a plurality of isolated pH ranges, optionally, narrow pH ranges. The pH ranges spanned by the plurality of isolated crystallization reactors may or may not overlap.

Another particular advantage of the method of the present invention is that protein crystals may be obtained from a protein solution that is not highly purified, since the method of the invention comprises isoelectric focusing which is directed to protein separation and resolution from impurities.

According to another aspect, the present invention provides an apparatus suitable for inducing rapid formation of biomolecule crystals, preferably proteins, comprising:

(a) a buffer chamber having an upper side and a lower side, the lower side being sealed with a bottom such that the buffer chamber encloses at least one buffer compartment capable of holding fluids;

(b) at least one crystallization reactor, the at least one crystallization reactor comprises an IEF buffer, the at least one crystallization reactor is contained within the buffer chamber;

(c) a device for generating an electrical field; and optionally, (d) means for circulating fluids contained within the buffer compartment.

According to one embodiment, the apparatus further comprises a holder having an upper side and a lower side, the holder encompasses the at least one crystallization reactor or adapted for supporting a substrate comprising the at least one crystallization reactor, said at least one crystallization reactor comprises an IEF buffer, the holder is contained within the buffer chamber. According to another embodiment, the holder is deployed within the at least one buffer compartment. According to a certain embodiment, the holder is a capillary comprising at least one crystallization reactor.

According to an alternative embodiment, the apparatus further comprises two salt bridges having two ends, one end of each salt bridge is in contact with one end of the holder and one end of each salt bridge is contained within the at least one buffer chamber. Preferably, the apparatus comprises two buffer chambers, each buffer chamber, such that each buffer chamber encloses one end of one salt bridge.

According to a preferred embodiment, the apparatus further comprises a temperature-controlled module enabling to manage the temperature at the at least one crystallization reactor.

According to an alternative embodiment, the holder encompasses at least one cavity, the at least one cavity containing a crystallization reactor comprising an IEF buffer.

According to yet another embodiment, the holder has plurality of cavities, such that each cavity is adapted for containing a crystallization reactor. According to some embodiments, the temperature of one crystallization reactor is different from the temperature of another crystallization reactor.

According to yet another embodiment, the holder comprises a material having a larger resistance than that of the polymer comprised within the crystallization reactor.

According to yet another embodiment, the holder comprises a non-conductive material. The non-conductive material may be selected from the group consisting of: poly-N-methyl methacrylamide, acrylic, lucite, polystyrene, ceramic, glass and poly-methyl-methacrylate.

According to yet another embodiment, the holder comprises a material that is impermeable to biomolecules in order to avoid diffusion of proteins from a crystallization reactor within one cavity to a crystallization reactor within any other cavity.

According to yet another embodiment, the at least one crystallization reactor further comprises a polymer, the polymer comprises at least one substance selected from the group consisting of: branched polymer, linear polymer, polyacrylamide, agarose, hydrogel, glycol polymer, cellulose, modified cellulose, cross-linked polyvinyl alcohol, cross-linked polyethylene oxide and glycol polymer.

According to yet another embodiment, the buffer chamber comprises a non-conductive material.

According to yet another embodiment, the apparatus of the present invention is adapted for monitoring under a microscope the formation of crystals within the at least one crystallization reactor.

According to another embodiment, the buffer compartment is adapted for holding a solution comprising running buffer and at least one biomolecule dissolved within the running buffer.

According to one embodiment, the present invention provides miniaturized and automated apparatus and method for high throughput rapid macromolecule crystallization. The apparatus of the present invention may be constructed to have automated interacting components, for example, titrators for filling of cavities with pre-polymerized crystallization reactors comprising IEF buffers (Immobilines, ampholytes etc.), extractors for recovering protein crystals from the cavities or the crystallization reactors, and devices for monitoring and recording the formation of protein crystals within the crystallization reactors.

These and further objects, features and advantages of the present invention will become apparent from the following detailed description and appended claims.

DETAILED DESCRIPTION OF THE INVENTION

Figure 1A:
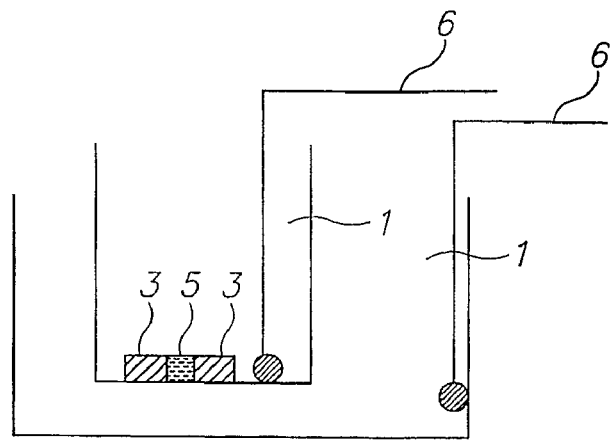
FIG. 1 is a schematic representation of various (A-C) crystallization systems comprising a buffer compartment (1) enclosed within a buffer chamber (2), a holder (3), electrodes (6), a salt bridge (10) and a solid support (7), a capillary (8) or a strip (14) comprising one or more crystallization reactors (5) and, optionally, a loading point (9).

The present invention provides methods and apparatus for inducing a rapid generation of protein crystals from a protein solution. The method of the present invention comprises isoelectric focusing and thereby formation of a concentrated protein solution or band which facilitates a rapid protein crystallization, typically within a period of no more than 15 hours.

All current methods used to grow protein crystals rely on tedious 'trial and error' experiments and searches for the optimal conditions that will result in the formation of a crystal. A review of the various factors affecting the crystallization of proteins has been published by McPherson, Methods Enzymol., 114, pp. 112-20 (1985). McPherson and Gilliland, J. Crystal Growth, 90, pp. 51-59 (1988) compiled lists of proteins and nucleic acids that have been crystallized, as well as the conditions under which they were crystallized. A compendium of crystals and crystallization recipes, as well as a repository of coordinates of solved protein and nucleic acid structures, is maintained by the Protein Data Bank at the Brookhaven National Laboratory [http//www.pdb.bnl.gov; Bernstein et al., J. Mol. Biol., 112, pp. 535-42 (1977)]. These references can be used to determine the conditions necessary for crystallization of a protein, as a prelude to the formation of appropriate protein crystals and can guide the crystallization strategy for other proteins. Alternatively, an intelligent trial and error search strategy can, in most instances, produce suitable crystallization conditions for many proteins, provided that an acceptable level of purity can be achieved for them [see, e.g., C. W. Carter, Jr. and C. W. Carter, J. Biol. Chem., 254, pp. 12219-23 (1979)].

In general, crystals are produced by combining the protein to be crystallized with an appropriate aqueous solvent or aqueous solvent containing appropriate crystallization agents, such as salts or organic solvents. The solvent is combined with the protein and may be subjected to agitation at a temperature determined experimentally to be appropriate for the induction of crystallization and acceptable for the maintenance of protein activity and stability. The solvent can optionally include co-solutes, such as divalent cations, cofactors or chaotropes, as well as buffer species to control pH. The need for co-solutes and their concentrations are determined experimentally to facilitate crystallization.

In an industrial-scale process, the controlled precipitation leading to crystallization can best be carried out by the simple combination of protein, precipitant, co-solutes and, optionally, buffers in a batch process. As another option, proteins may be crystallized by using protein precipitates as the starting material. In this case, protein precipitates are added to a crystallization solution and incubated until crystals form. Alternative laboratory crystallization methods, such as dialysis or vapor diffusion, can also be adopted. McPherson, ibid and Gilliland, ibid, include a comprehensive list of suitable conditions in their reviews of the crystallization literature.

Any protein having a defined isoelectric point may be used to prepare protein crystals according to the teaching of the present invention. It should be noted, however, that the conditions for crystallization, such as the content, density, viscosity, and other features of the IEF buffer as well as the temperature at the crystallization reactor among other setting parameters, can be optimized to yield the desired quality of crystals. Accordingly, it will be appreciated by those of skill in the art that some degree of adjustment of these feature and conditions may be necessary to provide crystals using the methods and apparatus of the present invention.

The terms a "protein crystal" or "crystal" are interchangeably used herein to describe protein molecules arranged in a crystal lattice. Protein crystals contain a pattern of specific protein-protein connections that are repeated periodically in three dimensions. The protein crystals of this invention do not include amorphous solid forms or precipitates of proteins, such as those obtained by lyophilizing a protein solution. Crystals display characteristic features including a lattice structure, characteristic shapes and optical properties such as refractive index and birefringence. A crystal consists of atoms arranged in a pattern that repeats periodically in three dimensions. In contrast, amorphous material is a non-crystalline solid form of matter, sometimes referred to as an amorphous precipitate. Such precipitates have no molecular lattice structure characteristic of the crystalline solid state and do not display birefringence or other spectroscopic characteristics typical of the crystalline forms of matter.

The terms "concentrated protein solution" or "concentrated solution" are interchangeably used herein to describe a medium comprising at least one protein wherein the concentration of the protein ranges from saturation, or even super saturation, to a concentration that is equivalent to about 50% saturation. If the IEF buffer is polymerized than the protein forms a band upon concentrating, accordingly the terms of "concentrated protein band" or "concentrated band" are used.

Typically, protein crystallization according to the present invention may be initiated with a protein solution, in a running buffer, the protein solution comprising at least one protein having a known isoelectric point (pI). The protein solution may be a dilute solution. Upon introduction of an electric field to the protein solution, the protein is driven into a crystallization reactor comprising IEF buffer having a pH range that overlaps with the pI of the protein. Thus, each protein molecule when driven into the volume of said reactor looses its charge and ceases moving in the electric field, resulting in a concentrated solution or band of uncharged proteins in the crystallization reactor. The process of electrophoretical accumulation and concentration of the protein, from the initially diluted solution, is very fast and efficient and typically occurs within a time span in the order of minutes, or even tens of minutes. The accumulating protein molecules spread out within the crystallization reactor by diffusion resulting in rapid crystal nucleation and growth therein.

An "isoelectric focusing" or "IEF" is a common separation techniques based on the net charge of the molecules, typically proteins, that are exposed to the IEF process. The net charge of a protein is determined from its amino acid content. Of the 20 amino acids found in typical proteins, four (aspartic and glutamic acids, cysteine and tyrosine) carry a negative charge and three (lysine, arginine and histidine) a positive charge, in some pH range. A specific protein, defined by its specific sequence of amino acids, is thus likely to incorporate a number of charged groups along its length. The magnitude of the charge contributed by each amino acid is governed by the prevailing pH of the surrounding solution, and can vary from a minimum of 0 to a maximum of 1 charge (positive or negative depending on the amino acid), according to a titration curve relating charge and pH according to the pK of the amino acid in question. Under denaturing conditions in which all of the amino acids are exposed, the total charge of the protein molecule is given approximately by the sum of the charges of its component amino acids, all at the prevailing solution pH.

IEF is a widely used electrophoresis method to separate proteins by their isoelectric point. IEF involves migration of charged proteins through a pH gradient established by a desired IEF buffer, typically within a gel, wherein protein migration is derived from or induced by an electric field. A protein with specific pI lose its charge, and thus stop migrating within the gel, upon reaching a location in the pH gradient gel having a pH that is equal to the protein's pI. At this location the protein accumulates. The advantage of IEF is the capability to resolve a plurality of proteins, each having a specific pI, into discrete bands directly from the protein mixture in solution. The final outcome of the classic IEF method is a plurality of pH bands, each pH band is loaded with a specific protein having a unique pI. Two proteins having different ratios of charged amino acids can be separated by virtue of their different net charges at some pH. Under the influence of an applied electric field, a more highly charged protein will move faster than a less highly charged protein of similar size and shape. If the proteins are made to move from a sample zone through a non-connecting medium (typically a gel such as polyacrylamide), an electrophoretic separation will result. If, in the course of migrating under an applied electric field, a protein enters a region whose pH has that value at which the protein's net charge is zero (the isoelectric pH), it will cease to migrate relative to the medium. Further, if the migration occurs through a monotonic pH gradient, the protein will "focus" at this isoelectric pH value. If it moves toward more acidic pH values, the protein will become more positively charged, and a properly-oriented electric field will propel the protein back towards the isoelectric point. Likewise, if the protein moves towards more basic pH values, it will become more negatively charged, and the same field will push it back toward the isoelectric point. This separation process, called isoelectric focusing, can resolve two proteins differing by less than a single charged amino acid among hundreds in the respective sequences.

A key requirement for an isoelectric focusing procedure is the formation of an appropriate spatial pH gradient. This can be achieved either dynamically, by including a heterogeneous mixture of charged molecules (ampholytes) into an initially homogeneous separation medium, or statically, by incorporating a spatial gradient of titrating groups into the gel matrix through which the migration will occur. The former represents classical ampholyte-based isoelectric focusing, and the latter the more recently developed immobilized pH gradient (IPG) isoelectric focusing technique. The IPG approach has the advantage that the pH gradient is fixed in the gel, while the ampholyte-based approach is susceptible to positional drift as the ampholyte molecules move in the applied electric field. The best current methodology combines the two approaches to provide a system where the pH gradient is spatially fixed but small amounts of ampholytes are present to decrease the adsorption of proteins onto the charged gel matrix of the IPG.

The compositional gradient required to form the desired pH gradient IPG gel is commonly produced from heavy gel monomer composition formulated to yield a basic pH, light gel monomer composition formulated to yield an acidic pH, a polymerization initiator such as ammonium persulfate, and a polymerization catalyst such as tetramethylethylenediamine (TEMED). Glycerol and deuterium oxide (heavy water) may be used to increase the density of the solutions, thus helping to stabilize the gradient formed in the mold through the interaction of the resulting density gradient and the earth's gravity. Several references describe automated devices for creating gradients of polymerizable monomers. Such systems have been used for making porosity gradient gels used in molecular weight separations of proteins. Altland et al. (Clin. Chem. 30(12 Pt 1):2098-2103, 1984) shows the use of such systems for creating the gradients of titratable monomers used in the creation of IPG gels. U.S. Pat. No. 4,169,036 describes a system for loading slab-gel holders for electrophoresis separation. discloses an automated apparatus for producing gradient gels are disclosed in U.S. Pat. Nos. 4,594,064; 6,554, 991 among others.

Rapid crystallization according to the present invention requires appropriate physical conditions to allow the working of the invention. Several factors within the method and apparatus of the present invention affect the kinetics of crystallization.

First, to ensure that the desired protein access the appropriate crystallization reactor, it is advantageous to speed up the kinetics of the molecules within the running buffer in order to increase the probability of any molecule to encounter with the crystallization reactor.

Advantageously, the movement of the proteins within the running buffer is increased as a result of the convection heat generated by the electrical field that is introduced according to the method of the present invention. It is contemplated that this enhanced kinetics of the proteins increases the probability that any protein will encounter and moreover will become trapped within a crystallization reactor that is immersed within the running buffer.

According to one embodiment, the velocity of the proteins within the running buffer is accelerated by a device that circulates the running buffer. Circulation can be typically achieved using a stir bars, pumps, vibrators, e.g., piezo vibrator, agitators, tilting devices or any agitation device and techniques known in the art. In another embodiment, the device for circulation can be a mechanism for moving the IEF buffer or crystallization reactors relative to the running buffer. For example, the IEF buffer or crystallization reactors can be rotated in the running buffer.

Alternatively, the methods of the invention are devoid of such a circulating device. In another embodiment of this invention, the circulation is solely provided by the convection currents naturally generated during the isoelectric focusing.

According to another embodiment, the amount of convection energy that is sufficient to circulate the biomolecule is $10^{-10}$ joules per 1 $cm^3$ of running buffer.

According to yet another embodiment, the method of the present invention comprises utilizing a rapid IEF procedure according to the principles disclosed in WO03/008977.

Second, to ensure that the desired protein accessing the appropriate crystallization reactor encounters said reactor, forms a concentrated protein solution or a concentrated protein band. Typically, the concentrated protein solution/band is generated within the crystallization reactor at the vicinity of the interface between the crystallization reactor and the external environment, the proteins then enter and diffuse within the crystallization reactor and consequently form protein crystals.

The viscosity and volume of the crystallization reactor are designed such that desired proteins can enter the reactor, diffuse therein and can further crystallize within the reactor. In cases where the IEF buffer within the crystallization reactor is in the form of a gel, then the porosity of the gel is further customized to obtain the desired crystal. Typical diffusion constants for proteins in gels are such that the diffusion time to spread the protein distribution to distances of the order of 0.1 mm is around 1000 sec (~20 min). Therefore the predicted time for crystal growth of crystals with comparable dimensions is of this order of magnitude.

Another important parameter, which influences crystallization efficiency, is the pH at the crystallization reactor. Shifting the pH value of the crystallization reactor slightly above or below the pI value of the biomolecule will cause the biomolecule to remain with a marginal charge after entering the reactor and thus with an additional mode of motion which the crystallization reactor.

Furthermore, the texture of the crystallization reactor has to be suitable for either isolation of the crystals for further applications or/and for collection of X-ray diffraction data of a crystal within a crystallization reactor.

Immobilized liquid membranes may be used in the construction of crystallization reactors. Particularly, immobilized liquid membranes may be used as an external envelope to the crystallization reactors of the invention, providing the reactors with boundaries of a selective permeability to desired biomolecules. Immobilized liquid membranes are typically confined within a microporous solid. One of the most widely used and simplest process of preparing porous membranes is the Gelgard™ process, in which the semicrystalline films or fibers are extruded from the melt. Porosity is induced by stretching solid-state polymer, like polypropylene. Pore sizes up to 0.04 µm are available as well as hollow fibers with 100-1500 µm ID and 25 µm wall thickness which are used for example, in blood oxygenators. Such immobilized liquid membranes are generally compatible with ethyl alcohol, ethylene glycol, and isopropyl alcohol. Another example of a widely used porous membrane is Gore-Tex™, a microporous poly (tetrafluoroethylene), which is also manufactured by stretching process, is chemically inert and is a hydrophobic synthetic polymeric membranes.

The dimensions of the crystallization reactor depend on the amount of desired proteins that is used and on the type of system and/or apparatus used. The volume of the crystallization reactor may be also designed to (1) facilitate the formation of a concentrated biomolecule solution/band within the reactor, typically at the vicinity of the interface between the reactor and the external environment; and (2) enable diffusion of the biomolecule therein and thereby enable crystallization of said biomolecules.

Third, the method of the present invention requires that there is only one protein species per crystallization reactor since the presence of irrelevant proteins or other impurities interferes with the desired crystallization process. To ensure that only one protein species enters a crystallization reactor, the pH range spanned in the crystallization reactor by the IEF buffer encompasses the pI of the one protein species. However, the methods of the present invention facilitate crystallization of any desired protein species even if said species is not purified. In the event that a non-purified protein solution is provided, it is required that at least one crystallization reactor would comprise an IEF buffer encompassing the pI of the desired protein species, wherein the pH range spanned in the crystallization reactor by the IEF buffer is sufficiently narrow, preferably ultra-narrow, thus avoiding crystallization of impurities.

Thus, according to a certain embodiment, the IEF buffer within each crystallization reactor has an extremely narrow pH range, e.g. 5.50-5.60 (0.1 pH unit or less difference) or ultra narrow pH range, e.g., 5.52-5.54 (0.02 pH unit difference or less). This is possible because an IEF buffer according to the invention can be one buffering agent that has been adjusted to a certain pH value. In this case, the pH range of the IEF buffer is equivalent to the buffering capacity of the buffering agent around the pH value to which the buffering agent had been adjusted. An example of an IEF buffer that may be used in accordance with the present invention is Tris Glycine (pH 8.20+/-0.05, Biorad, catalog number 161-0771).

The term "pH range" refers to the highest and to the lowest pH values in an IEF buffer (e.g., pH 7.9-pH 8.9), or the difference between the highest and lowest pH values in an IEF buffer (e.g., 1.0 pH units).

According to yet another embodiment, the pH ranges of the plurality of crystallization reactors do not overlap. According yet another embodiment, the pH step between one or more IEF buffers is no more than 0.1 pH units, preferably, no more than 0.02 pH units.

The terms "step" or "pH step" are interchangeable as used herein to describe the incremental difference in pH values between two different IEF buffers having different or partially different pH ranges. For example, if the pH step between crystallization reactor #1 and crystallization reactor #2 is 0.1 pH unit, than crystallization reactor #1 can have a pH gradient starting at pH 6.8 and ending at pH 7.8 and crystallization reactor #2 can have a pH gradient starting at pH 7.9 and ending at pH 8.9 (i.e., the difference between the lower limit of crystallization reactor #1, pH 7.9, and the upper limit of crystallization reactor #2, pH 7.8, corresponds to a step of 0.1 pH unit).

According to several embodiment, the pH steps between more than two crystallization reactors do not have to be uniform.

According to yet another embodiment, the intervals within a crystallization reactor do not have to be uniform. The term "interval" refers to the incremental difference between the pH values within the pH gradient created by the IEF buffer. For example, within a crystallization reactor, the intervals can be as small as 0.02 pH units through the full pH range in that reactor (e.g., pH 6.8, pH 6.82, pH 6.84, pH 6.86 and so on).

According to some embodiments, the intervals within a crystallization reactor do not have to be uniform.

According to one embodiment, the pH range of an IEF buffer in a crystallization reactor is relatively wide, e.g. more than one pH unit, alternatively more than two pH units. According to another embodiment, the pH range of an IEF buffer in a crystallization reactor is narrow, e.g., about one pH unit or less. According to yet another embodiment, the pH range of an IEF buffer in a crystallization reactor is ultra narrow, e.g. about 0.2 of a pH unit or less, alternatively about 0.02 of a pH unit or less.

According to one embodiment, the pH interval of an IEF buffer is 0.1 pH unit or less. According to another embodiment, the pH interval of an IEF buffer is 0.02 unit or less.

According to one embodiment of this invention, the pH steps between two or more IEF buffers are 0.01 units or less. According to another embodiment of this invention, the pH steps between two or more IEF buffers are 0.02 units or less.

According to one embodiment the present invention provides a method for rapid crystallization of biomolecules, comprising:
  (a) providing at least one biomolecule species;
  (b) providing at least one crystallization reactor comprising an IEF buffer having a pH range, the pH range comprises a pH corresponding to the pI of the at least one biomolecule species;
  (c) contacting said at least one biomolecule species and said at least one crystallization reactor;
  (d) introducing an electric field to the running buffer thereby generating within said at least one crystallization reactor a concentrated solution of said at least one biomolecule species; and
  (e) allowing said at least one biomolecule species in the concentrated solution to crystallize within the at least one crystallization reactor.

According to yet another embodiment, step (c) further comprises depositing the at least one biomolecule species and said at least one crystallization reactor in running buffer. According to yet another embodiment, step (c) further comprises stirring the running buffer. Advantageously, step (e) further comprises monitoring and/or detecting the formation of a biomolecule crystal.

Contacting the at least one biomolecule species and the at least one crystallization reactor according to step (c) of the method of the invention may be achieved in various ways. For example, in the event that the biomolecule is provided in a solution, contacting of the biomolecule solution and the at least one crystallization reactor may be achieved by applying one drop or more of the solution onto the crystallization reactor. The biomolecule solution may be applied onto a membrane, a matrix or any other absorbing substance which is laid over, put down or positioned onto a crystallization reactor in order to obtain a contact between the biomolecule and the crystallization reactor. If the biomolecule is provided in a gel segment, the gel segment is allowed to get in contact with at least one crystallization reactor.

According to yet another embodiment, step (c) of the method of the invention may further comprise deposition of the substantially connected biomolecule and at least one crystallization reactor within a solution of running buffer.

The term "biomolecule" as used herein refers to any compound, either man-made or natural, that has an observable effect on a cell, a cell component or an organism. This term applies to proteins, protein complexes comprising chemical entities, protein-DNA complexes, DNA, RNA, enzymes, peptides, polypeptides, antibodies, antigens, antigenic epitopes and variants thereof, polynucleotides, hormones, carbohydrates, lipids, phospholipids and biotinylated probes. The term "biomolecule" is often exemplified with the preferred embodiment of a "protein".

The terms "polypeptide", "peptide" and "protein" are used interchangeably to refer to polymers of amino acids of any length. These terms also apply to amino acid polymers in which one or more amino acid residues is an artificial chemical analogue of a corresponding naturally occurring amino acid, as well as to naturally occurring amino acid polymers. An amino acid polymer in which one or more amino acid residues is an "unnatural" amino acid, not corresponding to any naturally occurring amino acid, is also encompassed by the use of the terms "protein", "peptide" and "polypeptide" herein.

"Nucleic acid" or "polynucleotide" refer to a nucleotide sequence comprising a series of nucleic acids in a 5' to 3' phosphate diester linkage that may be either an RNA or a DNA sequence. If the nucleic acid is DNA, the nucleotide sequence is either single or double stranded. A nucleic acid encoding the protein of the invention is RNA or DNA that encodes a protein capable of binding cellulose with high affinity, is complementary to nucleic acid sequence encoding such protein, or hybridizes to nucleic acid sequence encoding such protein and remains stably bound to it under stringent conditions.

Any form of protein may be crystallized according to the method of this invention. The proteins may be glycoproteins, phosphoproteins, sulphoproteins, iodoproteins, methylated proteins, unmodified proteins or contain other modifications. Such proteins may be, for example, therapeutic proteins, prophylactic proteins, including antibodies, cleaning agent proteins, including detergent proteins, personal care proteins, including cosmetic proteins, veterinary proteins, food proteins, feed proteins, diagnostic proteins and decontamination proteins. Included among such proteins are enzymes, such as, for example, lysozymes, dehydrogenase, hydrolases, isomerases, lyases, ligases, adenylate cyclases, transferases and oxidoreductases. Examples of hydrolases include elastase, esterase, lipase, nitrilase, amylase, pectinase, hydantoinase, asparaginase, urease, subtilisin, thermolysin and other proteases and lysozyme. Examples of lyases include aldolases and hydroxynitrile lyase. Examples of oxidoreductases include peroxidase, laccase, glucose oxidase, alcohol dehydrogenase, glutamate dehydrogenase and other dehydrogenases. Other enzymes include cellulases and oxidases.

Examples of therapeutic or prophylactic proteins include hormones such as insulin, glucogon-like peptide 1 and parathyroid hormone, antibodies, inhibitors, growth factors, postridical hormones, nerve growth hormones, blood clotting factors, adhesion molecules, bone morphogenic proteins and lectins trophic factors, cytokines such as TGF-β, IL-2, IL-4, α-IFN, β-IFN, γ-IFN, TNF, IL-6, IL-8, lymphotoxin, IL-5, Migration inhibition factor, GMCSF, IL-7, IL-3, monocyte-macrophage colony stimulating factors, granulocyte colony stimulating factors, multidrug resistance proteins, other lymphokines, toxoids, erythropoietin, Factor VIII, amylin, TPA, dornase-α, α-1-antitripsin, human growth hormones, nerve growth hormones, bone morphogenic proteins, urease, toxoids, fertility hormones, FSH and LSH.

Therapeutic proteins, such as the following, are also included: leukocyte markers, such as CD2, CD3, CD4, CD5, CD6, CD7, CD8, CD11a, CD11b, CD11c, CD13, CD14, CD18, CD19, CE20, CD22, CD23, CD27 and its ligand, CD28 and its ligands B7.1, B7.2, B7.3, CD29 and its ligands, CD30 and its ligand, CD40 and its ligand gp39, CD44, CD45 and isoforms, Cdw52 (Campath antigen), CD56, CD58, CD69, CD72, CTLA4, LFA-1 and TCR histocompatibility antigens, such as MHC class I or II antigens, the Lewis Y antigens, SLex, SLey, SLea and SLeb; integrins, such as VLA-1, VLA-2, VLA-3, VLA-4, VLA-5, VLA-6 and LFA-1; adhesion molecules, such as Mac-1 and p150,95; selectins, such as L-selectin, P-selectin and E-selectin and their counter receptors VCAM-1, ICAM-1, ICAM-2 and LFA-3; interleukins, such as IL-1, IL-2, IL-3, IL-4, IL-5, IL-6, IL-7, IL-8, IL-10, IL-11, IL-12, IL-13, IL-14 and IL-15; interleukin receptors, such as IL-1R, IL-2R, IL-4R, IL-5R, IL-6R, IL-7R, IL-8R, IL-10R, IL-11R, IL-12R, IL-13R, IL-14R and IL-15R; chemokines, such as PF4, RANTES, MIP1α, MCP1, NAP-2, Gro α, Gro β, and IL-8; growth factors, such as TNF α, TGFβ, TSH, VEGF/VPF, PTHrP, EGF family, EGF, PDGF family, endothelin and gastrin releasing peptide (GRP); growth factor receptors, such as TNFalphaR, RGFbetaR, TSHR, VEGFR/VPFR, FGFR, EGFR, PTHrPR, PDGFR family, EPO-R; GCSF-R and other hematopoietic receptors; interferon receptors, such as IFN αR, IFNβR and IFNγR; immunoglobulins and their receptors, such as IgE, FceRI and FceRII; blood factors, such as complement C3b, complement C5a, complement C5b-9, Rh factor, fibrinogen, fibrin and myelin associated growth inhibitor.

The proteins that are crystallized according to the method of this invention may be any natural, synthetic or recombinant protein antigen including, for example, tetanus toxoid, diptheria toxoid, viral surface proteins, such as CMV glycoproteins B, H and gCIII, HIV-1 envelope glycoproteins, RSV envelope glycoproteins, HSV envelope glycoproteins, EBV envelope glycoproteins, VZV envelope glycoproteins, HPV envelope glycoproteins, Influenza virus glycoproteins, Hepatitis family surface antigens; viral structural proteins, viral enzymes, parasite proteins, parasite glycoproteins, parasite enzymes and bacterial proteins. Also included are tumor antigens, such as her2-neu, mucin, CEA and endosialin. Allergens, such as house dust mite antigen, lol p1 (grass) antigens and urushiol are included. Toxins, such as pseudomonas endotoxin and osteopontin/uropontin, snake venom and bee venom are included. Also included are glycoprotein tumor-associated antigens, for example, carcinoembryonic antigen (CEA), human mucins, her-2/neu and prostate-specific antigen (PSA; Henderson et al., Advances in Immunology, 62, pp. 217-56, 1996).

According to yet another embodiment, the at least one crystallization reactor comprises a polymer, the polymer comprises one or more substances selected from the group consisting of: linear polymers, branched polymers, polyacrylamide, agarose, hydrogels, cellulose, modified cellulose, cross-linked polyvinyl alcohol, cross-linked polyethylene oxide and glycol polymer. The crystallization reactors may comprise various monomers other than, or in addition to, the conventional acrylamide/bis-acrylamide solution or agarose solutions. It is known in conventional chemically polymerized gels to use hydroxyethylmethacrylate and other low-molecular weight acrylate-type compounds as monomers; these have been commercialized as "Lone-Ranger" gels. Use of polymers substituted with one or more acrylate-type groups has also been described in the literature (Zewert and Harrington, Electrophoresis 13: 824-831, 1992), as especially suitable for separations in mixed solvents of water with miscible organic solvents, such as alcohol or acetone. Gel forming monomers can also be any substantially water-soluble molecule containing a photo-polymerizable reactive group, in combination with a material which can form crosslinks, provided that the combination, once polymerized, forms a gel suitable for the particular type of electrophoresis.

Exemplary materials that may be added to the IEF buffer include acrylamide, in combination with methylene-bis-acrylamide or other known crosslinkers;hydroyethylmethacrylate and other low-molecular weight (less than about 300 daltons) derivatives of acrylic acid, methacrylic acid, and alkyl-substituted derivatives thereof, such as crotonic acid; vinyl pyrrolidone and other low-molecular weight vinyl and allyl compounds; vinylic, allylic, acrylic and methacrylic derivatives of nion-ionic polymers, including such derivatives of agarose ("Acrylaide" crosslinker, FMC Corp.), dextran, and other polysaccharides and derivatives, such as cellulose derivatives including hydroxyethyl cellulose; polyvinyl alcohol; monomeric, oligomeric and polymeric derivatives of glycols, including polymers of ethylene oxide, propylene oxide, butylen oxide, and copolymers thereof, acryl, vinyl or allyl derivatives of other water-compatible polymers, such as poly-HEMA (polyhydroxyethyl acrylic acid), polymeric N-isopropyl acrylamide (which is temperature-sensitive), maleic-acid polymers and copolymers, partially hydrolyzed EVAC (polymer of ethylene with vinyl acetate), ethyleneimine, polyaminoacids, polynucleotides, and copolymers of the subunits of these with each other and with more hydrophobic compounds such as pyridine, pyrrolidone, oxazolidine, styrene, and hydroxyacids. The polymerizable materials need not be entirely water-soluble, especially when solvents or surfactants are included in the gel forming solution.

Additionally or alternatively the IEF buffer may comprise derivatives of common polymers which may be prepared by methods known in the art. For example, addition of allyl glycidyl ether to hydroxyl groups is known, as is esterification of hydroxyls with acids, anhydrides or acyl chlorides, such as acrylic anhydride. Amines are readily derivatized with acyl anhydrides or chlorides.

Candidate non-acrylamide monomers can include, e.g., allyl alcohol, HEMA (hydroxyethyl [methyl] acrylate), polyethylene glycol monoacrylate, polyethylene glycol diacrylate, ethylene glycol monoacrylate, ethylene glycol diacrylate, vinylcaprolactam, vinylpyrrolidone, allylglycidyl dextran, allylglycidyl derivatives of polyvinylalcohol and of cellulose and derivatives, vinyl acetate, and other molecules containing one or more acryl, vinyl or allyl groups.

According to one embodiment, the crystallization reactor comprises a polymerized IEF buffer having dimensions, such as a diameter of about 20 µm to about 5 mm; and a length of about 0.5 mm to about 10 mm. Preferably, a crystallization reactor comprising a polymerized buffer maintains its structure when immersed in a buffer solution within a buffer compartment and particularly maintains its structure when the buffer solution is subjected to the influence of an electric field.

In the event that the crystallization reactor comprises a polymerized IEF buffer, during IEF procedure a concentrated band of biomolecule species is formed at the vicinity of the interface between the crystallization reactor and the external environment, if the isoelectric point (pI) of the biomolecule species falls within the pH range spanned by the IEF buffer. The biomolecule species within the band then diffuse within the crystallization reactor and, unexpectedly, rapid crystal growth is initiated.

As detailed above, the polymer of the crystallization reactor may be any well known and typical gel-forming material known to be suitable for electrophoresis purposes. Such materials include gel-forming polymers which are sufficiently chemically reactive to enable the introduction of ionisable radicals i.e. acid groups such as carboxylic, sulphonic, phosphonic groups and nitrogenous basic groups such as amino groups. Typical suitable materials are hydroxylic polymers including cellulose, modified cellulose, cross-linked polyvinyl alcohol and cross-linked polyethylene oxide. Cross-linked polyacrylamide gels suitably chemically modified, agar or agarose gels may also be used. Crystallization reactors comprising a polymerized IEF buffer may be generally prepared by providing a buffer that is polymerized by the addition of a polymer, using polymers and methods as known in the art of electrophoresis. See e.g., Sambrook, et al. (1989) Electrophoresis buffers in Molecular Cloning (Nolan, C. ed.), Cold Spring Harbor Laboratory Press, NY, pp. B.23-24.

According to yet another embodiment, the at least one crystallization reactor is joined to a solid substrate. Conveniently, the crystallization reactors may be supported on a substrate, for example, porous carrier substrates such as filter-paper, cotton or linen cloth, or other suitable web materials to provide adequate strength. Additionally, some cross-linking of the agar or agarose gels is advisable to withstand the influence of an electric field.

According to yet another embodiment, the at least one crystallization reactor is provided within a capillary. Normally, a crystal for collection of diffraction patterns by X-ray crystallography is carefully separated from its crystallization medium and inserted into a capillary tube. The tube is sealed from the air using dental wax or silicone grease, along with a small amount of crystallization medium inside to maintain hydration (McPherson et al., Krieger Publishing, Malabar, p. 214, 1989). Applying the method of the present invention by using crystallization reactors in a capillary, does not According to yet another embodiment, the method of the invention comprises providing a plurality of crystallization reactors. According to yet another embodiment, the plurality of crystallization reactors are linked, joined, or substantially contiguous to a solid substrate in a spatially addressable manner. According to yet another embodiment, the method of the invention comprises obtaining a plurality of crystals, wherein the plurality of crystals may be formed at the same crystallization reactor or at different crystallization reactors comprised within one apparatus. A plurality of crystals at different crystallization reactors comprised within one apparatus may be formed substantially at the same time and/or substantially under the same crystallization setup. Thus, the methods and apparatus of the invention are suitable for high throughput crystallization of various biomolecules at the same time and/or under similar conditions and/or setups.

A "solid substrate" or "holder" or "matrix" are interchangeably used herein with reference to an inert supporting element which comprises at least one crystallization reactor. This element may be a strip, a membrane, a chip, a sheet or any other supporting configuration which comprises the at least one crystallization reactor.

According to yet another embodiment, the holder comprises a material having a larger resistance than that of the polymer comprised within the crystallization reactor.

According to yet another embodiment, the holder comprises a non-conductive material. The non-conductive material may be selected from the group consisting of: poly-N-methyl methacrylamide, acrylic, lucite, polystyrene.

According to yet another embodiment, the holder comprises a material that is impermeable to biomolecules in order to avoid diffusion of proteins from a crystallization reactor within one cavity to a crystallization reactor within any other cavity.

A holder according to this invention is a solid material or a semi-solid material, e.g., a ceramic, a glass, polystyrene, poly (methyl methacrylate) such as lucite, or a gel, that may comprises one or a plurality of crystallization reactors or may comprises one or a plurality of cavities adapted for comprising crystallization reactors. According to one embodiment, the material forming the holder is poorly conductive. According to another embodiment, the holder is, in part or in whole, made of a material that is biomolecule impermeable and ion impermeable. A crystallization reactor can be set on the surface of the holder e.g., as a gel or as a gel linked, joined, or substantially contiguous to a substrate, or can be set in a groove etched in the holder or can extend through the holder as long as the crystallization reactor can contact the running buffer. The holder can be movable or immobilized within the buffer chamber of the apparatus of the invention.

According to one embodiment of the invention, if the crystallization reactor extends through the matrix, then, one side of the crystallization reactor is in contact with the running buffer, that side is preferably covered with a layer made of a biomolecule-impermeable material.

The holder comprising a plurality of cavities wherein each cavity essentially containing a crystallization reactor, can be made, for example, by drilling hole(s) or channel(s) through one side of the holder out through to the opposing side of the holder, filling the channel with a polymer, such as agarose or polyacrylamide gel, mixed with an IEF buffer that solidifies into a gel having a predetermined pH range. The grooves in the holder may not extend through the opposing side of the holder. The grooves can be made on any side of the holder. According to one embodiment, the grooves are on one side of the holder.

According to yet another embodiment, the method of the invention comprises providing a plurality of crystallization reactors comprising similar or different IEF buffers. According to yet another embodiment, the pH ranges of the plurality of crystallization reactors do not overlap.

According to yet another embodiment, a solid substrate comprising a plurality of crystallization reactors is selected from the group consisting of: immobilized pH gradient (IPG) strips, such as ProteomIQ™ IPG strips (Proteome systems), Servalyt Precotes™ gel (Invitrogen, Inc.), pH membranes and commercial pre-cast gels (e.g. Invitrogen, Inc., Amersham Pharmacia Biotech, Stratagene, Amresco Inc., Bio-Rad Laboratories and others) with the proviso that the arrangement of plurality of crystallization reactors meets, or is modified to meet, the principles of the present invention. Preferably, according to the present invention a plurality of crystallization reactors forms a non-continuous array of reactors, each reactor comprises an IEF buffer having a pH range wherein the pH range spanned by each IEF buffer may, or man not, overlap with the pH range of another IEF buffer in the non-continuous array.

According to some embodiments, the method of the invention provides a plurality of crystallization reactors comprising polymerized IEF buffer. The plurality of crystallization reactors may be identical, or each crystallization reactor may comprise a different gel (polymer). Optionally, the plurality of crystallization reactors comprises the same polymer at different concentrations resulting in a plurality of crystallization reactors exhibiting different permeabilities (e.g. different pore sizes), texture and viscosities among others.

Commercial IPG strips may be used for the working of the present invention providing that each IPG strip comprises a plurality of isolated pH bands, each pH band comprises a pH range. However the disadvantage of commercial IPG strips is that the volume and shape of each distinct pH band is not generally suitable for the formation of crystal, particularly since diffusion of biomolecules is limited within the bands. Thus, custom-made IPG strips are particularly suitable for obtaining crystals according to the principles of the present invention. The design of the custom-made strips is optimized to facilitate concentration, diffusion and crystallization of biomolecules therein.

The custom-made IPG strips are typically prepared in accordance with current practice for the preparation of thin planar IPG gel configuration bonded to an inert substrate, typically a sheet of Mylar plastic which has been treated so as to chemically bond to an acrylamide gel (e.g., Gelbond™ PAG film, FMC Corporation). The IPG gel is typically formed as a rectangular plate 0.5 mm thick, 10 to 30 cm long (in the direction of separation) and about 10 cm wide. Multiple samples can be applied to such a gel in parallel lanes, with the attendant problem of diffusion of proteins between lanes producing cross contamination. In the case where it is important that all applied protein in a given lane is recovered in that lane (as is typically the case in 2-D electrophoresis), it has proven necessary to split the gel into narrow strips (typically 3 mm wide), each of which can then be run as a separate gel. Since the protein of a sample is then confined to the volume of the gel represented by the single strip, it will all be recovered in that strip. Isoelectric focusing separation of proteins in IPG techniques is extensively described in the art. The concept of the IPG is disclosed in U.S. Pat. No. 4,130,470 and is further described in numerous later publications.

Alternatively, a crystallization reactor comprising a polymerized IEF buffer can be attached to a holder by linking reagents, such as disclosed in U.S. Pat. No. 4,243,507.

The term "IEF buffer" as used herein, refers to a buffer comprising components that have a buffering capacity around a given pH value (buffering agent) or components that organize to form a pH gradient (e.g., ampholytes, Immobilines or a combination of buffering agents).

The IEF buffer according to the present invention may be in the form of a viscous liquid or slurry or a gel such that a proteins can migrate in an electric field through the IEF buffer unless the pI of the protein is in the pH range of the IEF buffer. An IEF buffer according to this invention can comprise other components such as urea, detergent and a reducing agent as needed. It is desirable that the IEF buffers according to this invention are functionally stable under the influence of an electric field.

The term "viscous liquid" as used herein refers to a liquid or other media having an optimized viscosity, which facilitates diffusion of macromolecules within the viscous liquid with minimal, preferably with the absence, of convective motion and minimal to null sedimentation.

The IEF buffer and crystallization reactors comprising same can be formed by hand or by various devices. For example, the IEF buffer can be deposited (e.g., coated, printed or spotted) on the surface of a substrate, and may be immobilized onto the surface, or deposited in a groove or channel of a substrate. The substrate can be a matrix, such as a membrane, or a bead made of the same material as the matrix.

The IEF buffer can be made by a device that mixes an acidic and basic solution to form a buffer having the desired pH value ("titrator"). For the purpose of polymerization the buffer may be farther combined with a monomer (e.g., acrylamide) and a polymerizing agent and loaded into another device (e.g., a cavity) that lays the IEF buffer in a desired position.

According to one embodiment, ampholines used to generate the IEF buffer of the present invention are a set of various oligo-amino and/or oligocarboxylic acids that are amphoteric (i.e., positively charged in acidic media and negatively charged in basic media), soluble and have Mr values from approximately 300 up to 1000 u. Ampholytes used in this invention can be prepared or purchased. For example, several carrier ampholytes are known in the art (e.g., pages 31-50, Righetti, P. G., (1983) Isoelectric Focusing: Theory, Methodology and Applications, Eds., Work and Burdon, Elsevier Science Publishers B. V., Amsterdam; U.S. Pat. No. 3,485, 736). Alternatively, purchased ampholytes include Ampholines (LKB), Servalytes (Serva), Biolytes or Pharmalytes (Amersham Pharmacia Biotech, Uppsala, Sweden).

Immobilines may also be used to generate the IEF solutions of the present invention. Immobilines are non-amphoteric, bifunctional acrylamide derivatives of the general formula: $CH_2=CH-CO-NH-R$. Immobilines that are useful according to the present invention can be prepared or purchased. Methods for synthesizing Immobilines are known in the art, for example, Bjellquist et al., (J. Biochem. Biophys. Methods, 6: 317, 1983). The Immobilines can be copolymerized with the acrylamide to form crystallization reactors consisting of immobilized pH gradients. pH gradients according to the present invention can be formed by mixing amphoteric or non-amphoteric buffers. For example, such buffers combinations are described in Allen, RC et al., Gel Electrophoresis and Isoelectric Focusing of Proteins: Selected Techniques, Berlin: Walter de Gruyter & Co. (1984) and in U.S. Pat. No. 5,447,612 (Bier). Some IEF buffering agents include those are selected from the group consisting of: (1) 50 mM glycine, 14 mM NaOH; (2) 50 mM HEPES, 12 mM NaOH; (3) 50 mM THMA, 44.6 mM HC1; (4) 52 mM citrate acid, 96 mM $Na_2HPO_4$; (5) 50 mM BICINE, 18 mM NaOH; and (6) 50 mM DMGA, 40 mM NaOH. The pH gradient created by the IEF buffer in each cell can have a narrow or a wide pH range (e.g., pH 6.8-pH 7.8 or pH 6.8-pH 12.8, respectively).

The electric field used in the method of the invention and generated by the power supply of the apparatus and method of the invention may me of any voltage that the method and apparatus can tolerate, e.g. 100 to 10000 volt, or 500 to 10000 volt, or 500 to 5000 volt, provided the generated heat can be dissipated throughout the compartment comprising the running buffer and can be regulated by proper cooling. The voltage being supplied can be DC or AC. Power supplies and electrodes that can supply DC and AC currents are commercially available and known in the art.

According to one embodiment, the temperature of the running solution is maintained within the range of 0-30° C., and the electric field is between 50 V/cm to 2000 V/cm.

According to yet another embodiment, the electric field is selected from the group consisting of: an alternating electric field, a direct electric field. If the crystallization reactor comprising the IEF buffer is closed so that the electrical current is preventing from exiting out the opposite side of its entry into the crystallization reactor, then, according to one embodiment, the electric field is reversible. If the crystallization reactor is open, then the electrical field can be either direct, that is, unidirectional or alternating.

The terms "buffer" or "buffer solution" or "running buffer" are interchangeably used to describe a solution comprising, on the one hand, either a weak acid (such a carbonic acid) together with one of the salts of this acid or with at least one acid salt of a weak acid; or, on the other hand, a weak base (as ammonia) together with one of the salts of the base. Having these components, a buffer is capable of establishing the pH of the solution in accordance with the concentration of each of the component. A buffer is further capable of maintaining the established pH even upon the addition of acids or bases due to its resistance to change in hydrogen-ion concentration. The ability of a given buffer to establish and maintain a pH is also termed a "buffering capacity".

According to yet another embodiment, a solution of an isolated essentially pure protein may be used in the present invention to obtain protein crystals. Pure proteins may be obtained by any suitable protein purification method known in the art and include those described in Deutscher (Meth. Enzymology, 182:83-89, 1990) and in Scopes (Protein Purification: Principles and Practice, Springer-Verlag, N.Y., 1982). Protein purification includes isolation of a desired protein from other biological material, such as from cellular elements of cells transformed with recombinant nucleic acids encoding the desired protein. For example, purification can be achieved by employing immunoaffinity chromatography, e.g., using antibodies that specifically bind to the desired protein.

The terms "non-purified protein" and "not highly-purified protein" are interchangeably used herein to describe a protein which has not been completely separated from components that are not part of its structure or components that do not accompany it in its natural state. Typically, a purified protein comprises about 60 to 90% W/W of the pure protein within a protein sample, about 95%, and about 99%. The proteins used in the present invention are not necessarily highly purified prior to the IEF procedure.

According to one embodiment, the present invention provides a method for resolving multiple proteins and rapidly crystallizing a selected protein, comprising:
 (a) providing a solution comprising at least one biomolecule species;
 (b) resolving the solution by electrophoresis on a substrate, thereby obtaining at least one band in the substrate corresponding to at least one biomolecule species;
 (c) separating a portion from the substrate, the portion comprising the at least one band resolved in (b);
 (d) providing at least one crystallization reactor comprising an IEF buffer having a pH range, the pH range comprises the pI of said at least one band;
 (e) joining said at least one band to the at least one crystallization reactor;
 (f) introducing an electric field to the running buffer thereby generating within said at least one crystallization reactor a concentrated solution of the at least one biomolecule species resolved in (b); and
 (g) allowing said at least one biomolecule species in the concentrated solution of (f) to crystallize within the at least one crystallization reactor.

According to yet another embodiment, According to yet another embodiment, step (e) further comprises depositing the joined at least one band to the at least one crystallization reactor in running buffer. Preferably, the step (e) further comprises stirring of the running buffer. Advantageously, step (g) further comprises monitoring and/or detecting the formation of a protein crystal.

Monitoring and detecting crystal formation may be achieved by any one of the following: a device for detecting the biomolecules of the sample in crystallization reactor; a device for receiving the data from the detection device; and a device for processing the data received. According to one embodiment, a scanning microdensitometer detects, receives and processes the signal from the crystallization reactor.

One or more of the devices necessary for detecting the biomolecules of the sample in the crystallization reactor(s), receiving the data from the detection device, and processing the data received can be packaged into a computer.

A detection device can be designed to project electromagnetic radiation that is a spectrum of wavelengths, a plurality of wavelengths or one wavelength onto a lane simultaneously or sequentially. According to one embodiment, the illuminating light source is monochromatic. For example, the detection device can be a custom made photometer that quickly, sequentially reads the absorption magnitude from each crystallization reactor at a specific wavelength after a narrow spectrum of light is projected onto each reactor. Alternatively, the detection device can be designed to read each reactor simultaneously and/or take readings relating to the electromagnetic radiation emitted from each reactor at several wavelengths.

Suitable detection devices, including, but not limited to, the naked eye, spectrophotometric, chemiluminescent, photometric/densitometric, electrochemical or radiochemical detecting instruments depending on whether the biomolecule is labeled and the type of label. The label can require other components to cause a reaction that produces a signal or to enhance the signal that is detectable according to the abovementioned methods. A detailed discussion of suitable signal producing systems can be found in U.S. Pat. No. 5,185,243. Details of techniques for attaching labels are known in the art. See, for example, Matthews, et al., Anal. Biochem. (1985) 151: 205-209 and European Patent Application No. 0302175.

According to yet another embodiment, the solution of step (b) is resolved by isoelectric focusing on a substrate, thereby obtaining at least one band within the substrate corresponding to an isoelectric point of at least one biomolecule species.

According to yet another embodiment, the IEF buffer of step (d) has a pH range of no more than 0.2 pH units, preferably no more than 0.1 pH units, more preferably of no more than 0.02 pH units.

According to one embodiment, the methods of the present invention are carried out such that the temperature of the running solution is maintained within the range of 0-30° C. According to another embodiment, the temperature of the running solution is maintained within the range of 0-30° C., and the electric field is between 50 V/cm to 2000 V/cm.

According to yet another embodiment, the present invention provides a plurality of crystallization reactors wherein the temperature at each crystallization reactor is independent, preferably different, from the temperature of any other crystallization reactor. Temperature is one of the parameters that may be modulated in order to optimize diffusion and crystal growth in the method of the present invention.

Various commercially available temperature-controlled modules may be adapted for use in the context of the present invention. Exemplary suitable modules are automated thermal cyclers designed for robotic Polymerase Chain Reactions (PCRs), which may be modified in order to fit the requirements of the present invention. For example, the thermal cyclers of MJ Research (NJR, Waltham, Mass.; e.g. DNA Engine™, Dyad™, Mini-Cycler, PTC-100™, Tetrad™) feature Peltier heating and Alpha™ modules, which are interchangeable heating blocks that allow users to change sample format rapidly. Some of these cyclers feature Hot Bonnet™ heated lids and can be used for a variety of sample formats including microwell plates and even microscope slides. Another suitable system is the Smart Cycler® instrument (Cepheid, Sunnyvale, Calif.). The system is based on the company's I-CORE®0 technology-microfluidics-based, temperature-controlled modules that permit each sample to be subjected to different experimental conditions. Stratagene's RoboCycler (La Jolla, Calif.) offers another suitable temperature controlled modulus. The RoboCycler features four programmable blocks and offers a gradient feature to simplify optimization. This cycler unique is that it employs a robotic arm to move samples from block to block, wherein the temperatures in each block may be distinct.

A series of disclosures have dealt with various configurations of opening ("sample wells") used for loading macromolecules and macromolecular-containing samples to the surfaces of gels, most frequently slab gels used for protein or nucleic acid separations. In each case, these sample wells are designed to concentrate macromolecules in the sample into a thin starting zone prior to their migration through the resolving gel. The following references describe the use of devices placed against a gel to form wells: U.S. Pat. No. 5,304,292 describes the use of pieces of compressible gasket to form well walls at the top of a slab where the ends of the pieces touch the top edge-of the slab. U.S. Pat. No. 5,164,065 describes a shark's tooth comb used in combination with DNA sequencing gels.

Apparatus for Rapid Crystallization

The present invention also provides apparatus for rapid crystallization. According to yet another embodiment the present invention provides an apparatus suitable for inducing rapid formation of protein crystals, comprising:

(a) at least one crystallization reactor, the at least one crystallization reactor comprises an IEF buffer, the at least one crystallization reactor is contained within the buffer chamber;

(b) a device for generating an electrical field; and optionally, (c) means for circulating fluids contained within the buffer compartment.

According to one embodiment, the apparatus further comprises a holder having an upper side and a lower side, the holder encompasses the at least one crystallization reactor or adapted for supporting a substrate comprising the at least one crystallization reactor, said at least one crystallization reactor comprises an IEF buffer, the holder is contained within the buffer chamber. According to another embodiment, the holder is deployed within the at least one buffer compartment. According to a certain embodiment, the holder is a capillary comprising at least one crystallization reactor.

According to yet another embodiment, the apparatus further comprising two salt bridges having two ends, one end of each salt bridge is in contact with one end of the holder and one end of each salt bridge is contained within the at least one buffer chamber. Preferably, the apparatus comprising two buffer chambers, each buffer chamber, such that each buffer chamber encloses one end of one salt bridge.

Typically, a salt bridge functions as an ionic conductor, and is usually arranged between at least one crystallization reactor comprising a biomolecule solution or element(s) containing thereof, such as a holder and/or a substrate, and the buffer within the buffer compartment. Examples of salt bridges suitable for the apparatus of the present invention include glass, ceramic material or plastic tubes filled with an ionic conductor that may be obtained by dissolving an electrolyte such as potassium chloride or potassium nitrate in an agar.

According to another embodiment, the buffer compartment is adapted for holding a solution comprising a running buffer and at least one biomolecule species dissolved within the running buffer.

According to yet another embodiment, the holder has at least one cavity wherein the at least one cavity is adapted for holding a crystallization reactor comprising an IEF buffer and a polymer.

According to yet another embodiment, the holder comprises a plurality of cavities, each cavity comprises a crystallization reactor comprising a polymer and an IEF buffer.

According to yet another embodiment, the pH ranges of the IEF buffers within the plurality of crystallization reactors do not overlap.

The holder comprising a plurality of crystallization reactors in the apparatus of the kind described may be arranged in any desired configuration, for example either as a horizontal series of crystallization reactors arranged side by side and separated by the customary spacers or as a vertical series.

Figure 1B:
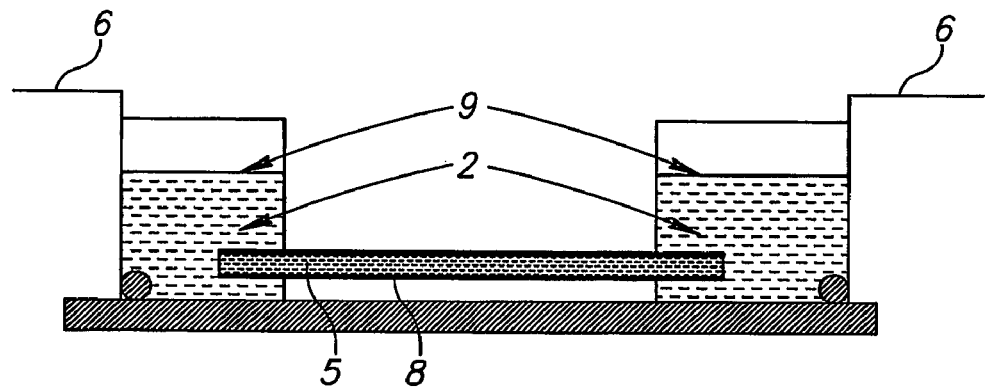
Figure 1C:
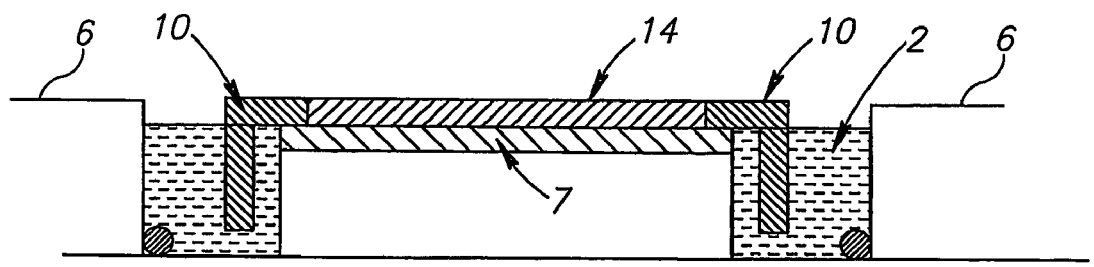

Referring now to FIG. 1 the apparatus of the invention comprises a buffer chamber containing a couple of electrodes, i.e. an anode and a cathode, and running buffer. The apparatus further contains crystallization reactors comprising an immobilines buffer FIG. (1A), crystallization reactors within a capillary (FIG. 1B) or customized IPG strip comprising a plurality of distinct and isolated pH bands (FIG. 1C).

Figure 2:
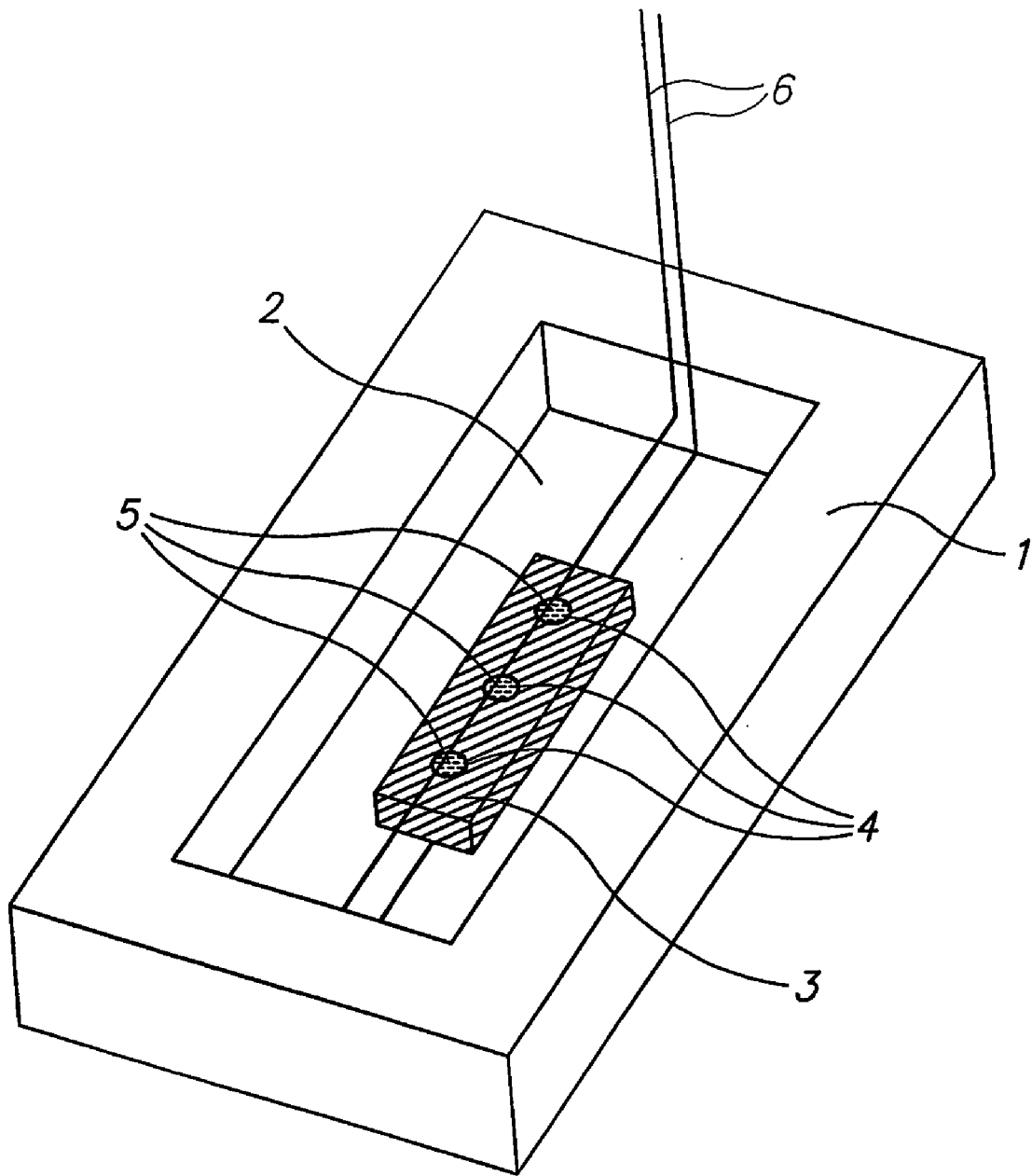
FIG. 2 is a schematic representation of a crystallization apparatus comprising a buffer compartment (1) enclosed within a buffer chamber (2), a holder (3), a plurality of cavities (4) comprising crystallization reactors (5) and electrodes (6).
Figure 3A:
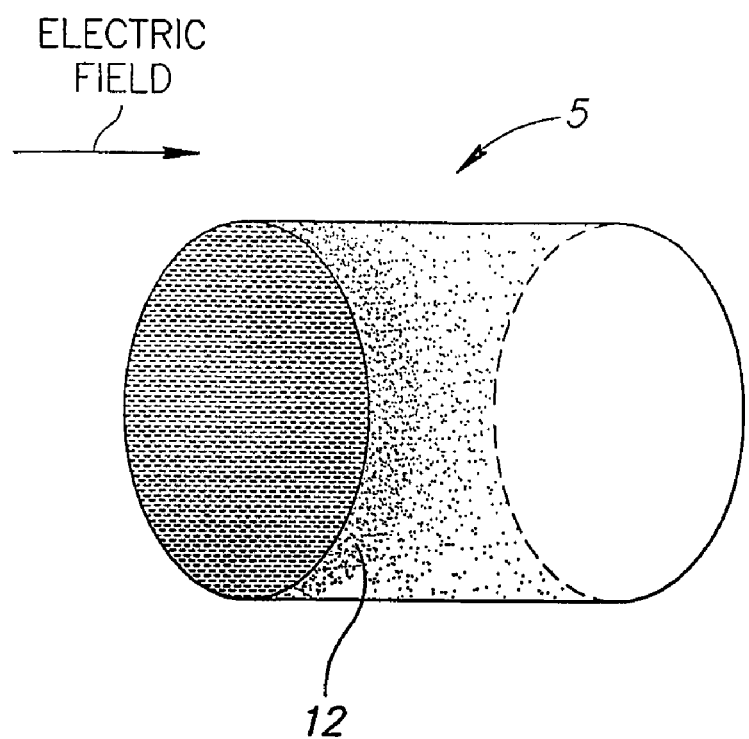
FIG. 3 is (A) a scheme describing protein migration from a protein band (12) within a crystallization reactor (5) contained in a holder (3) and (B) are cross-sectional schemes describing the top view (left scheme) and the side view of a holder (3) comprising three crystallization reactors.
Figure 3B:
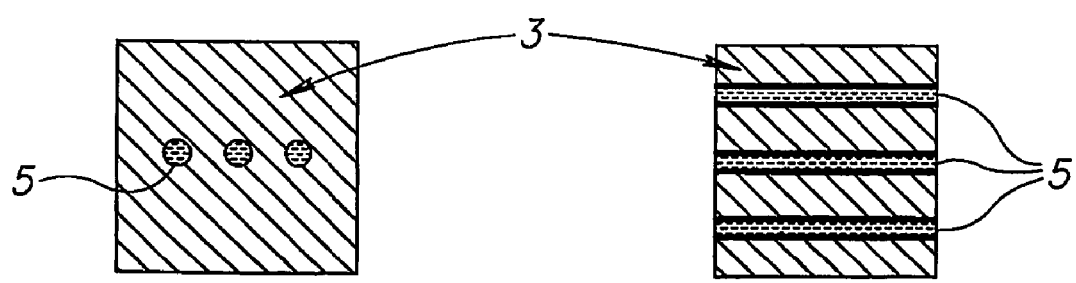

Referring now to FIGS. 2 and 3, the apparatus of the invention comprises a buffer compartment (1) enclosed within a buffer chamber (2), a holder (3), a plurality of cavities (4) comprising crystallization reactors (5) and electrodes (6).

According to one embodiment, the apparatus of the present invention comprises a plurality of crystallization reactors, each crystallization reactor comprises an IEF buffer, optionally the IEF buffer is polymerized. The pH upper and lower limits of the pH ranges created by the plurality of the IEF buffers may be different or identical. For example, the IEF buffer in crystallization reactor #1 can have a pH range starting at pH 6. 8 and ending at pH 7.8 and the IEF buffer in crystallization reactor #2 can have a pH range starting at pH 7.9 and ending at pH 8. 9. Further, the pH steps between an IEF buffer in crystallization reactor #1 and crystallization reactor #2 can be of different or of identical pI units.

According to yet another embodiment, the pH range of the IEF buffer may be wide, narrow or ultra-narrow, e.g., spanning 0.1 pH units or less, 0.02 pH units or less, or 0.01 pH units or less.

According to yet another embodiment, the IEF procedure is conducted using the apparatus of the invention wherein buffer compartment comprising the running buffer further comprises a holder encompassing a plurality of cavities containing a plurality of crystallization reactors comprising IEF buffers. Using this setup, the plurality of cavities are isolated from each other by a physical separation that substantially prevents the movement of biomolecules directly from one crystallization reactor to another rather than through the running buffer. Thus, the biomolecules primarily move through the running buffer from one crystallization reactor to another. In another embodiment, the crystallization reactors encompass the same or different pH ranges. In yet another embodiment, the present invention comprises a vast number of discrete, isolated crystallization reactors having substantially non-overlapping pH ranges such that a plurality of distinct proteins can be crystallized using a single setup. Moreover, using the apparatus, systems and methods of the present invention, wherein the crystallization reactors encompassing IEF buffers having narrow, preferably ultra narrow, pH ranges, it is feasible to crystallize in a single setup a plurality of distinct proteins having pI values that are 0.02 pH or less units apart, due to the great resolution capability of the method of the invention, particularly in comparison to the traditional IEF gel.

According to one configuration of the system, diffusion of biomolecule from one crystallization reactor into an adjoining crystallization reactor is avoided, e.g., between crystallization reactors that comprise IEF buffers with slightly different pH ranges, by using the apparatus of the present invention provided that the holder that encompass the crystallization reactors comprises a material that is impermeable to biomolecules.

The following nomenclature is used for the components of the apparatus of the invention as they appear throughout the specification and in the claims which follow: The terms "buffer chamber" or "running buffer chamber" may be used interchangeably, and denotes the container or reservoir which holds the buffer comprising the protein solution. The terms "matrix" or "chip" or "array" or "holder" may be used interchangeably, and denote the element comprising the crystallization reactor(s).

Applications of Rapid Crystallization

Rapid macromolecules crystallization is of great industrial value for storage, drug design and drug delivery. There is also an industrial need for preparation of large quantities of crystalline macromolecules. Non of the crystallization process known in the art are suitable for industrial-scale processing as there is always the risk that a crystal will not grow and in the event that a crystal indeed begins to grow, the long time that is requires to obtain a crystal of a desired size is not practical.

The motivations for creating rapid and efficient techniques for large-scale macromolecule crystallization, and particularly protein crystallization, are:

First, it is desirable to produce macromolecules in the crystalline state that are pure. Such crystals constitute a particularly advantageous form of proteins or nucleic acids for dosage preparations of therapeutics and vaccines. The present invention provides rapid methods for crystallizing macromolecules. Large-scale crystallization can be introduced as a final purification step and/or concentration step in clinical manufacturing processes, such as those for manufacturing therapeutics and vaccines. Moreover, large-scale crystallization can replace some of the purification steps in the manufacturing process. For example, protein crystallization can streamline the production of protein formulations making it more affordable.

Second, storage of macromolecule crystals is advantageous over storage of solutions, since macromolecular interactions which occur in solution are prevented or severely reduced in the crystalline state, due to considerable reduction of all reaction rates. Thus, the crystalline state is uniquely suited to the storage of mixtures of biological macromolecules. Shelf life of crystals may be further extended by encapsulating the crystals within a matrix comprising a polymeric carrier to form a composition as disclosed in U.S. Pat. No. 6,541,606. The composition enhances preservation of the native biologically active tertiary structure of the proteins and creates a reservoir which can slowly release active protein where and when it is needed.

Third, solid crystalline preparations can be easily reconstituted to generate ready to use parenteral formulations having very high protein concentration. Such protein concentrations are considered to be particularly useful where the formulation is intended for subcutaneous administration, see for example International Patent Publication No. WO 97/04801. For subcutaneous administration, injection volumes of 1.5 ml or less are well tolerated. Thus, for proteins that are dosed at 1 mg/kg on a weekly basis a protein concentration of at least 50 mg/ml is required and 100-200 mg/ml is preferred. These concentrations are difficult to achieve in liquid formulations, due to the aggregation problems. They can easily be achieved using protein crystals that are obtained by the methods of the present invention.

Fourth, protein crystals also constitute a particularly advantageous form for pharmaceutical dosage preparation.

The crystals may be used as a basis for slow release formulations in vivo. As those of skill in the art will appreciate, particle size is of importance for the dissolution of crystals and release of activity. It is also known that the rate of release is more predictable if the crystals have substantially uniform particle size and do not contain amorphous precipitate, see for example European Patent No. 265,214. Thus, protein crystals may be advantageously used on implantable devices, see for example International Patent Publication No. WO 96/40049. Implant reservoirs are generally on the order of 25-250 µl. With this volume restriction, a formulation of high concentration (greater than 10%) and a minimum amount of suspension vehicle is preferred. Protein crystals obtained by the method of the present invention may be easily formulated in non-aqueous suspensions in such high concentrations.

Fifth, another advantage of crystals is that certain variables can be manipulated to modulate the release of macromolecules over time. For example, crystal size, shape, formulation with excipients that effect dissolution, crosslinking, level of crosslinking and encapsulation into a polymer matrix can all be manipulated to produce delivery vehicles for biological molecules.

The present invention provides the above-described needs. The following advantages of the method of the present invention makes it suitable for high throughput industrial crystallization of macromolecules:
1. Capability to grow crystals from small diluted, and not necessarily purified, protein samples.
2. A concentrated protein solution or a concentrated protein band is created rapidly, within hours and even within a few minutes.
3. The macromolecules that accumulate in the crystallization reactors are uncharged or possess a very small charge, thus electrostatic repulsion is negligible or absent.
4. No sedimentation, convection or precipitation takes part during the formation of the concentrated macromolecule solution or during crystal formation.
5. Crystal growth may be extremely fast, within the order of minutes or hours.
6. In-process purification of the protein sample during the crystallization process, by the IEF element of the method excludes impurities and possible contamination by other isoforms and thus the method enables working with less purified protein samples, relative to the existing crystallization methods.
7. The option to apply the method of the invention using crystallization reactors within a capillary is specifically suitable for crystallography as there is no need to transfer the crystal from the reactor to a different environment. Such transfer is risking the crystal's structure and stability.

The forgoing advantages of the method of the present invention render it suitable for simultaneous separation and crystallization of individual isoforms of a given protein.

According to one embodiment, the present invention provides miniaturized and automated apparatus and method for high throughput rapid macromolecule crystallization. The apparatus of the present invention may be constructed to have automated interacting components, for example, titrators for filling of cavities with pre-polymerized crystallization reactors comprising IEF buffers (Immobilines, ampholytes etc.), extractors for recovering protein crystals from the cavities or the crystallization reactors, and devices for monitoring and recording the formation of protein crystals within the crystallization reactors.

Further stability of the crystals formed in accordance with the principles of the present invention may be achieved by any method known in the art for this purpose. For example, the crystals may be encapsulated as disclosed in U.S. Pat. No. 6,541,606, or inserted into a capillary tube which is then sealed from the air using dental wax or silicone grease, along with a small amount of crystallization buffer inside to maintain hydration (McPherson et al., ibid).

Optimization of the crystallization process according to the method and apparatus of the present invention may be obtained through a single experiment using several crystallization reactors with different gel concentrations (pore diameter, diffusion constant) and various protein dilutions. Each crystallization reactor may be also exposed to a different temperature.

EXAMPLES

Example 1

Crystallizing a Component of the p53 Protein

Three protein samples were supplied:
(a) p53 human DBD [pI (theoretical)=8.83]
(b) β-transcription factor from C Elegans [pI(theoretical)= 5.98]
(c) human β-transcription factor-[pI(theoretical)=5.5]

Figure 4:
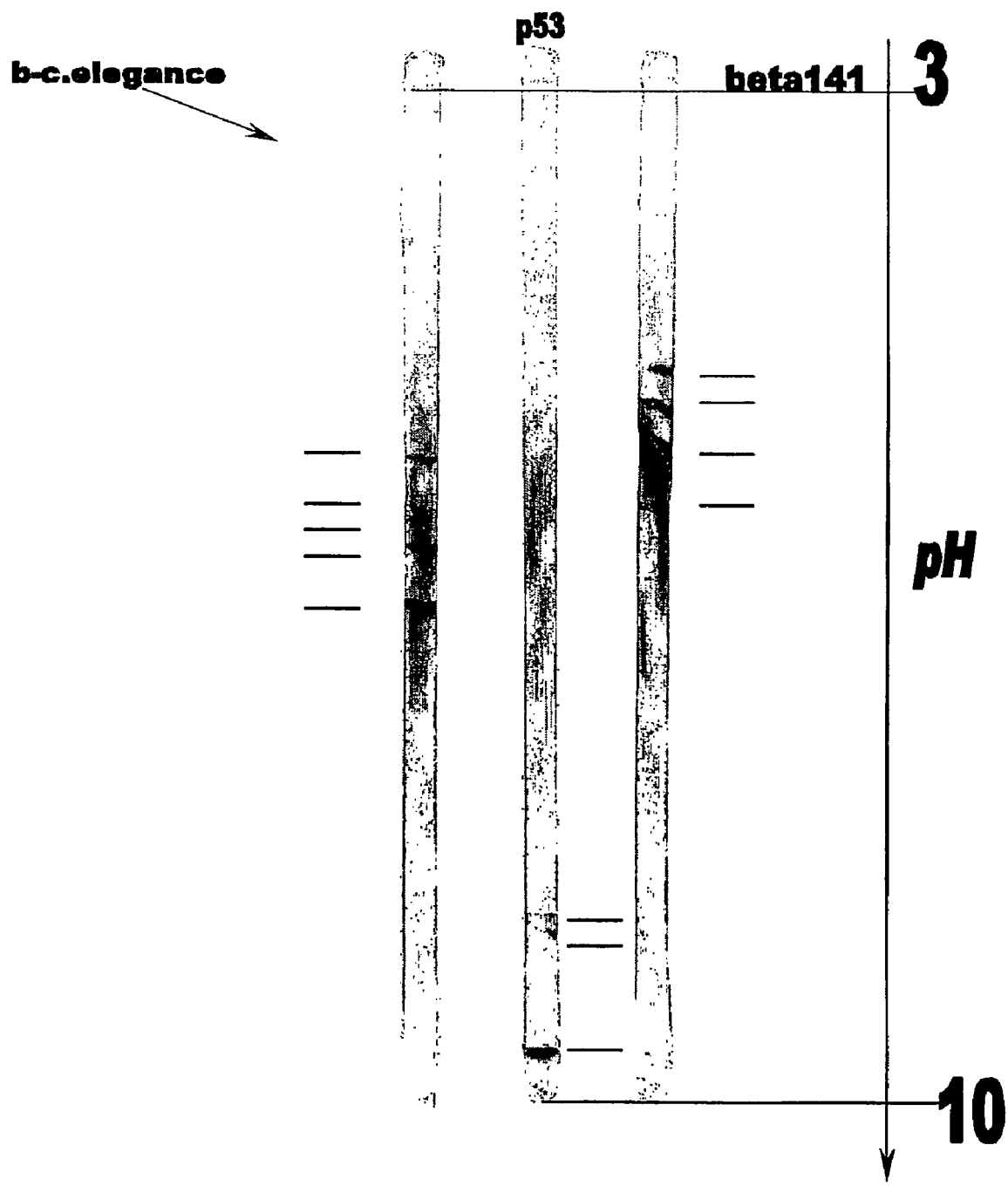
FIG. 4 presents separation of three protein samples by IEF on commercial IPG strips (Amersham Biosciences) of pH ranges from 3 to 10.

All three samples were analyzed by an initial IEF on commercial IPG strips pH 3-10 (Amersham) to determine the pH of the specific protein (FIG. 4). As can be seen in FIG. 4, each one of the three "purified" protein solutions was found to be composed of a large number of different protein bands.

For crystallization according to the method of the invention, a band corresponding to a certain pI of a specific protein was selected. Crystallization was carried out using a homemade IPG strip with pH values in the vicinity of the theoretical pI and an apparatus as schematically described in FIG. 4C. A few crystals were rapidly formed. The crystals were extracted from the IPG gel and the scattering pattern obtained for the p53 sample was indeed characteristic of multi-crystal sample with 2.8 Angstrom resolution.

Example 2

Figure 5:
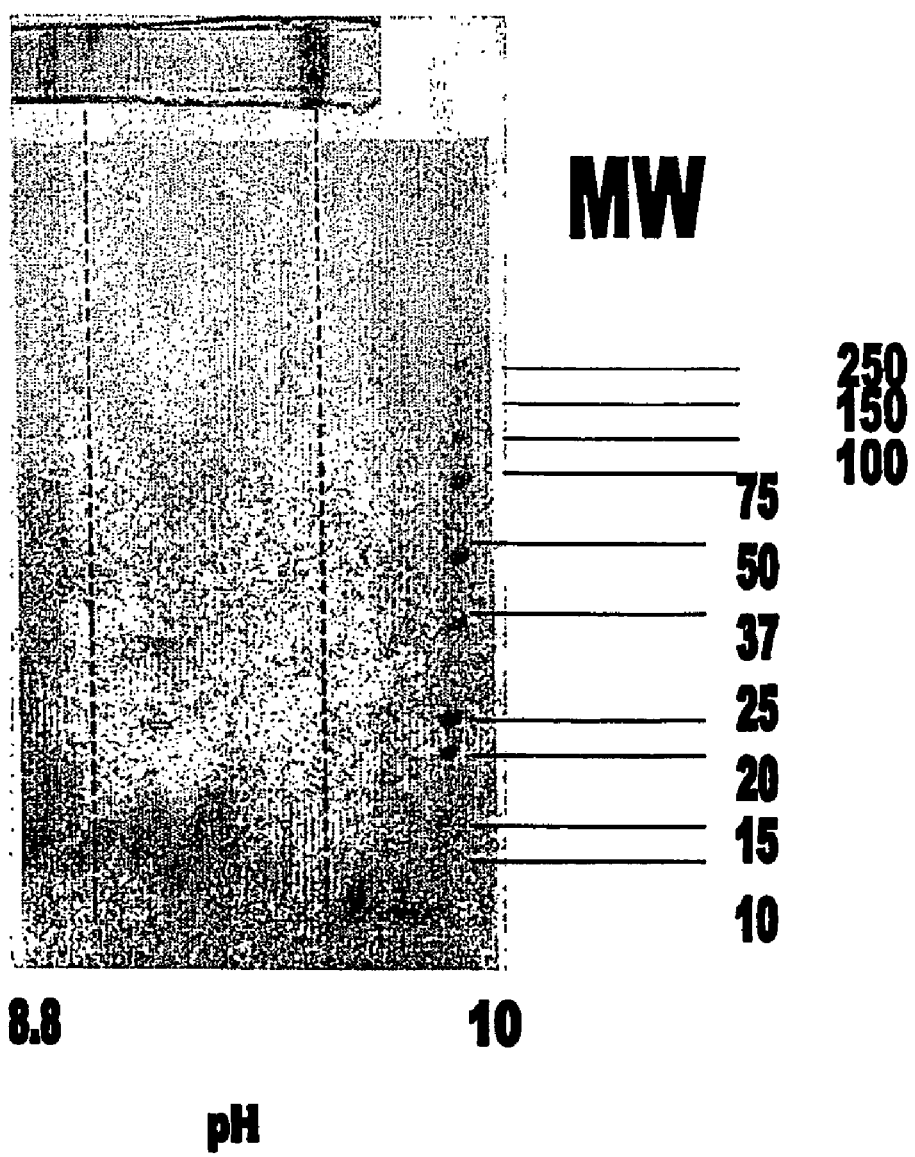
FIG. 5 shows separation and rapid crystallization of a protein obtained from the IPG strip of FIG. 1, using the method of the invention with an IEF buffer having narrow pH range of 9.5 to 9.75.

Feasibility Demonstration of Crystallization of an IEF Separated Protein by Using an IPG Zoom Strip Since our crystallization technique requires only microgram quantities of proteins, separation by IEF can serve as a source of material to obtain crystals. Such an experiment was performed on one of the bands separated from the p53 sample as seen in FIG. 5.

Figure 6:
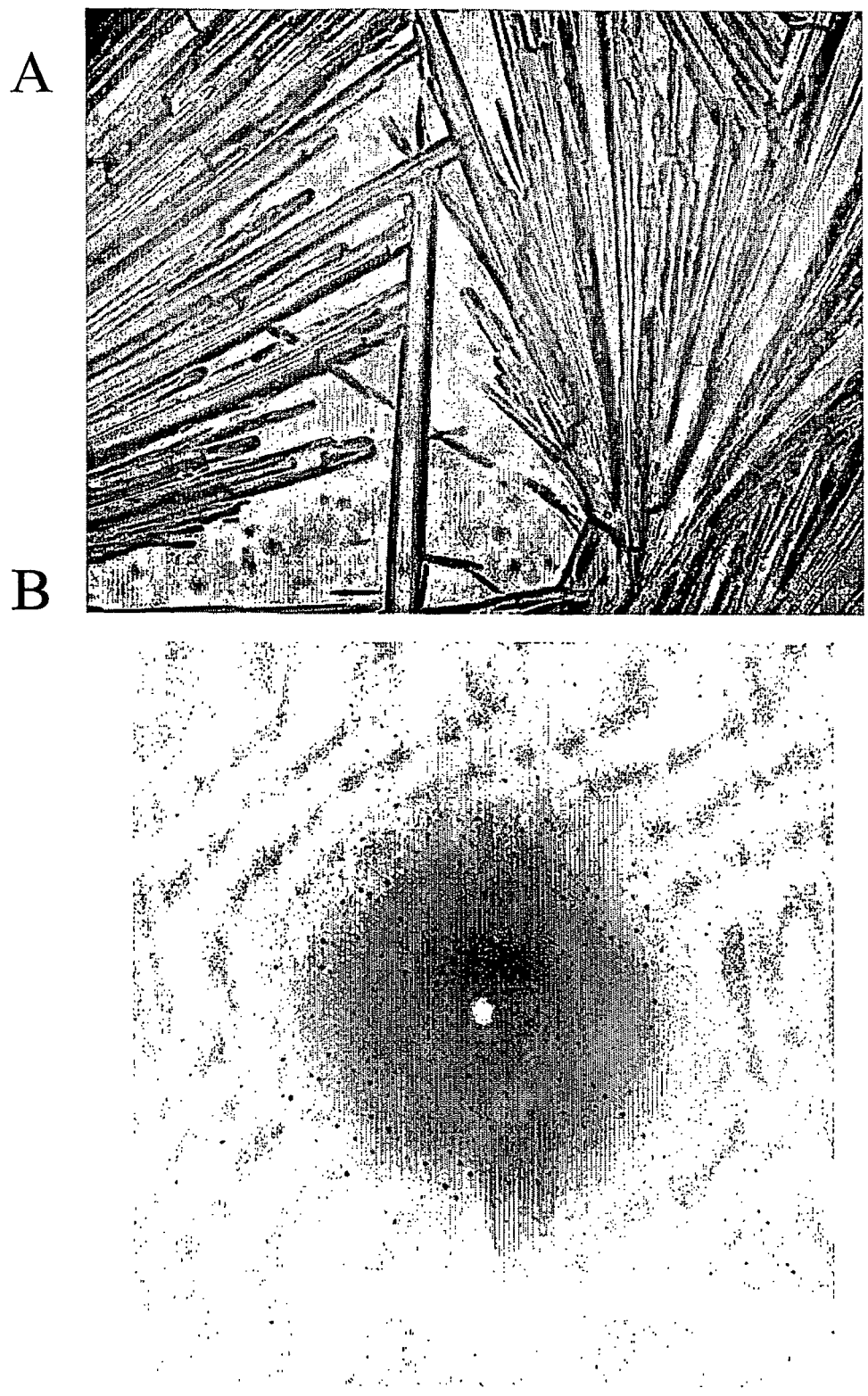
FIG. 6 exhibits a p53 crystal (A) obtained by the method of the invention and the diffraction pattern thereof (B).

The following procedure was employed: from the IPG strip we selected and cut out the band at pH~9.6, for crystallization we chose to utilize the system presented in FIG. 4C. For that purpose a short IPG zoom strip was prepared in the range of 9.5-9.75 in steps of 0.05. The strip was prepared by standard density gradient method. The protein band cut out from the IEF experiment was glued on with polyacrylamide close to the edge of the IPG strip. The strip was placed on top of the electrophoresis chamber shown in FIG. 4C. A standard IEF procedure resulted in focusing and crystallization of the separated fraction generating high quality crystals, as demonstrated in FIG. 6A. A diffraction pattern demonstrating resolution of 2.4 Angstroms is shown in FIG. 6B.

Example 3

Myoglobin Crystallization

Horse Heart Myoglobin (75 μg) was dissolved in 1.5 ml of water and introduced into the crystallization apparatus. This solution served as the running buffer (pH=7.00) for the IEF procedure. Immobiline™ buffer (Amersham) was polymerized into 10% polyacrylamide gel cylindrical cavities of 1 mm diameter and 1 mm depth (pH=6.80). An IEF separation was performed under the following conditions: 1200V, 30 min and distance between electrodes of 0.5 cm.

IEF was performed under intensive shaking of the apparatus, at 4° C., in order to facilitate protein migration within the buffer solution. An efficiency calibration which was conducted for the IEF procedure, indicated that the amount of protein, which was accumulated in the gel cavity, was about 50% of the total protein in the solution.

Figure 7:
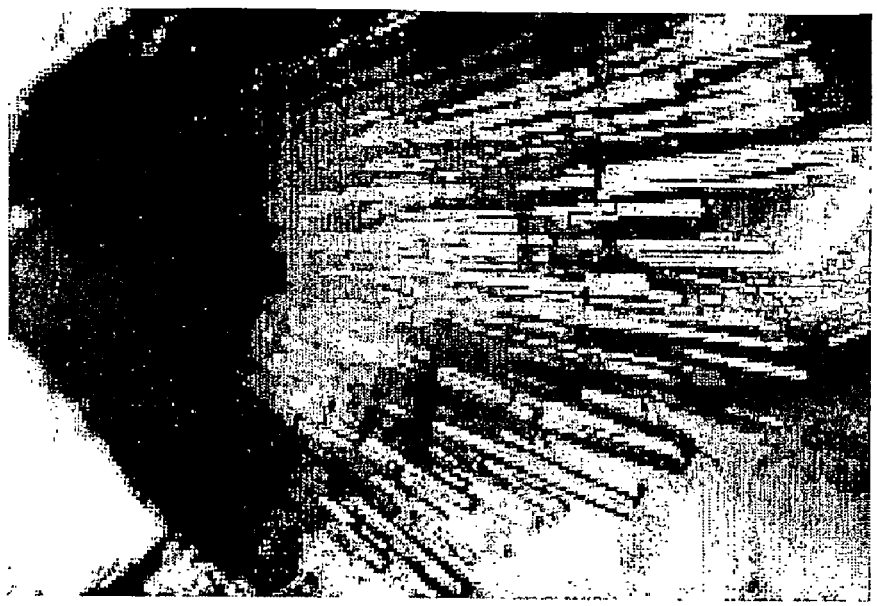
FIG. 7 demonstrates (A) an image (300 µm×150 µm) of a single myoglobin protein crystal, about 100 µm long, obtained in a crystallization reactor and (B) an image of hemoglobin crystal in gel. The elongated object at the center is the Hemoglobin crystal which is about 400 µm long.
Figure 7:
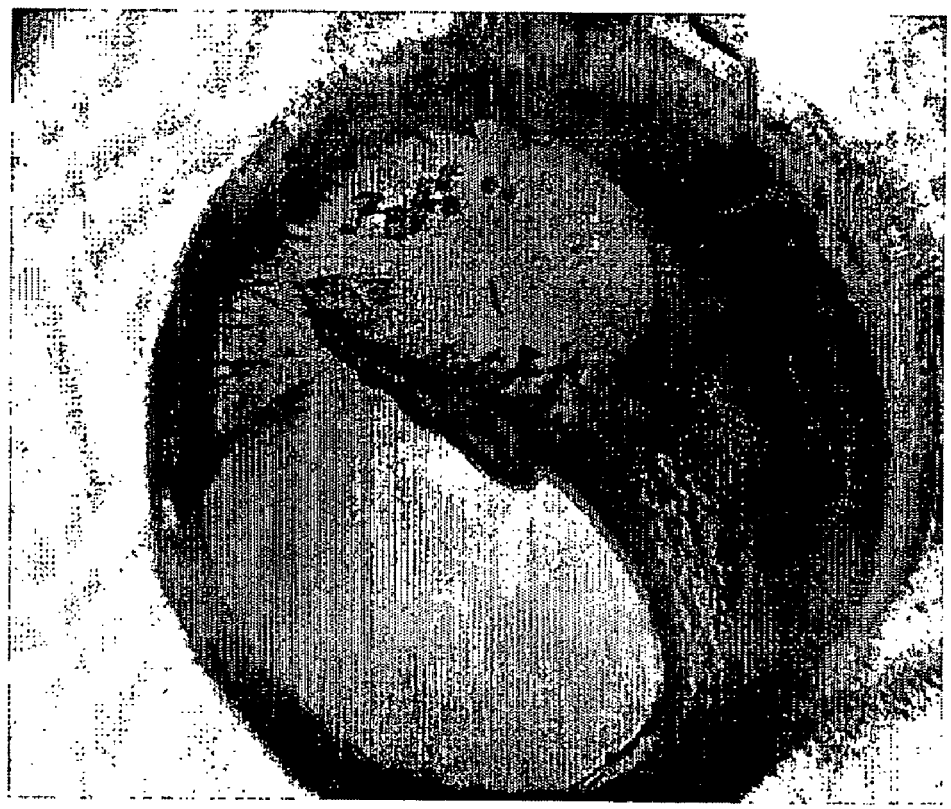

Inspection of the gel cavity under a microscope, revealed a highly developed crystalline structure in the gel (FIG. 7A).

Example 4

Hemoglobin S Crystallization

A solution of Hemoglobin S (1 μg/ml in water; Sigma), pI=7.0, was concentrated by isoelectric focusing into a pH buffer (Immobiline™ in 4% polyacrylamide gel) having a pH range of 6.9-7.05. An electric field of 1000V/cm was applied for 30 min under a temperature of 25° C. After 30 min. a crystal, 400 μm long, was obtained (FIG. 7B).

Example 5

Phycocyanine Crystallization

Figure 8:
FIG. 8 shows images of phycocyanin crystal (A) and of alcohol dehydrogenase crystal (B) within gel.
Figure 8:

A commercial Phycocyanin (1 μg; Sigma), having a pI of about 4.5 in a solution of 1 μg /ml, was subjected to IEF procedure in a pH buffer (Immobiline™ in 4% polyacrylamide gel) having a pH range of 4.4-4.6. The isofocusing conditions were: 25° C., an electric field of 100 V/cm and 30 min of experimental time. After 30 min. a crystal was obtained (FIG. 8A).

Figure 9:
FIG. 9 presents (A) an image of a glutamate dehydrogenase (GDH) crystal extracted from a gel within a cavity and (B) an image of a crystal of Aquaporin 3 in gel.
Figure 9:

Similarly, crystals of alcohol dehydrogenase (FIG. 8B) and glutamate dehydrogenase (GDH; FIG. 9A) were obtained.

Example 6

Crystallization of Aquaporin 3

Membrane proteins are generally regarded as most important proteins for structure determination. Unfortunately, most standards methods for protein crystallization fail to generate crystals of membrane proteins. The current example demonstrates the capability of the method of invention to allow crystallization of Aquaporin, which is one of the most important membrane proteins.

A solution of rat Aquaporin 3 (1 μg/ml; Alpha Diagnostic International) of pI=6.7 in a running buffer containing water and Ampholine™ (Amersham) was applied for the crystallization procedure. Concentration procedure, of the protein in pH gel cavities (4% polyacrylamide, pH 6.65-6.8), was performed by IEF using the following conditions: 40 min experimental time, 25° C. and 100 V/cm. The resulting crystal is presented in FIG. 9B.

Example 7

Crystallization of Bovine Carbonic Anhydrase

Figure 10:
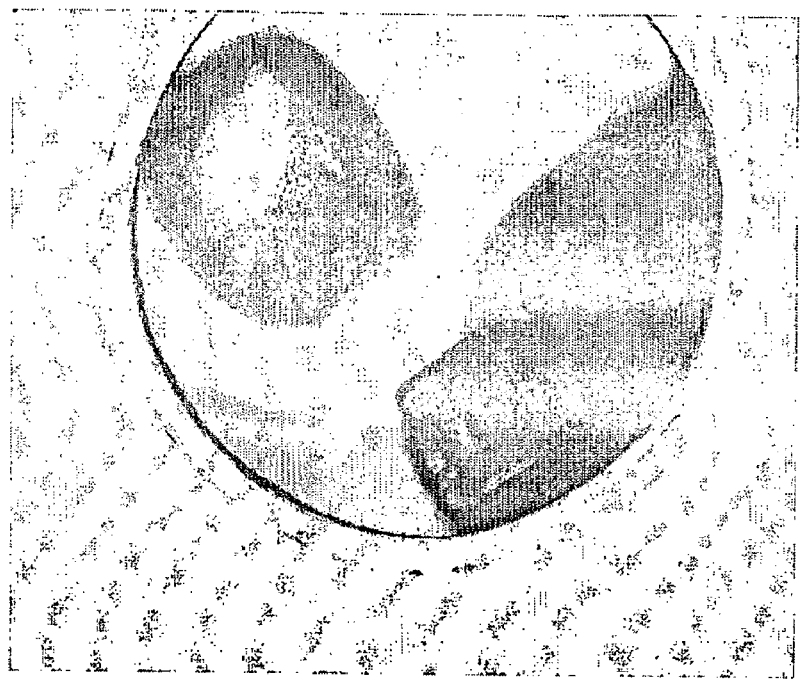
FIG. 10 presents images of a carbonic anhydrase crystal within a crystallization reactor consisting of a polymerized IEF buffer (A) and crystals extracted from the crystallization reactor (B).
Figure 10:
Figure 11:
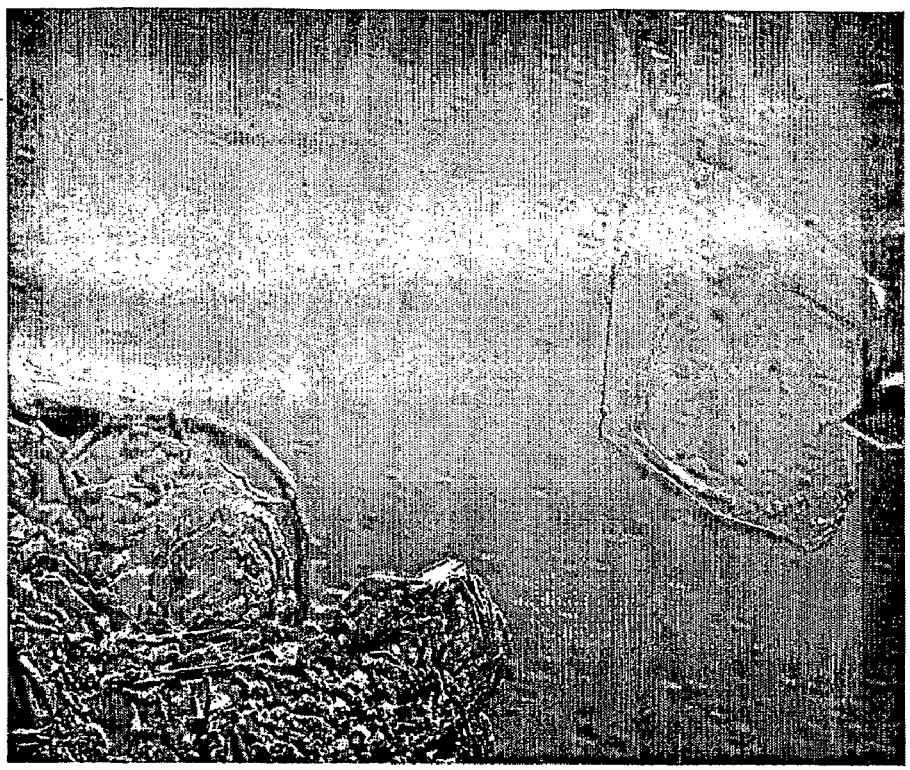
FIG. 11 presents images of the diffraction pattern (A) of a pepsin-4 crystal (B).
Figure 11:
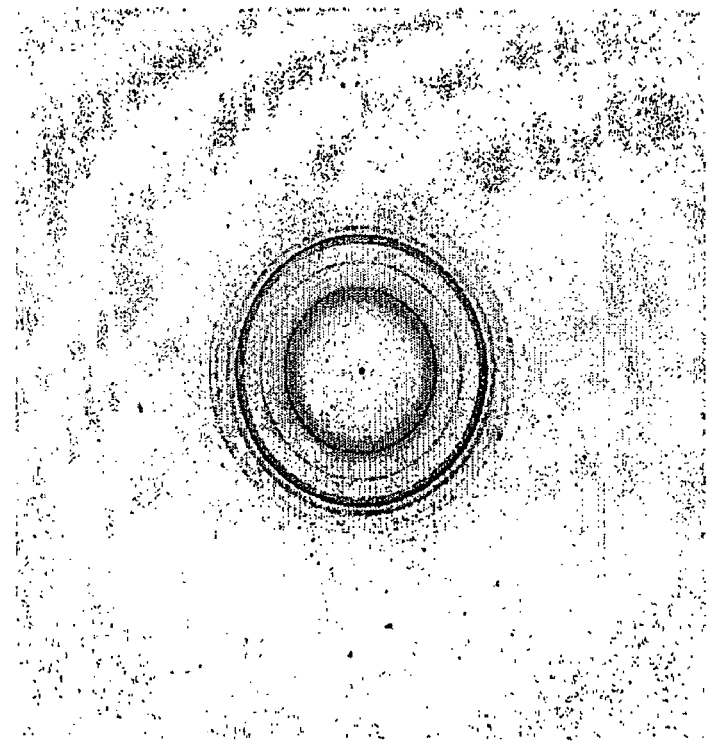
Figure 12:
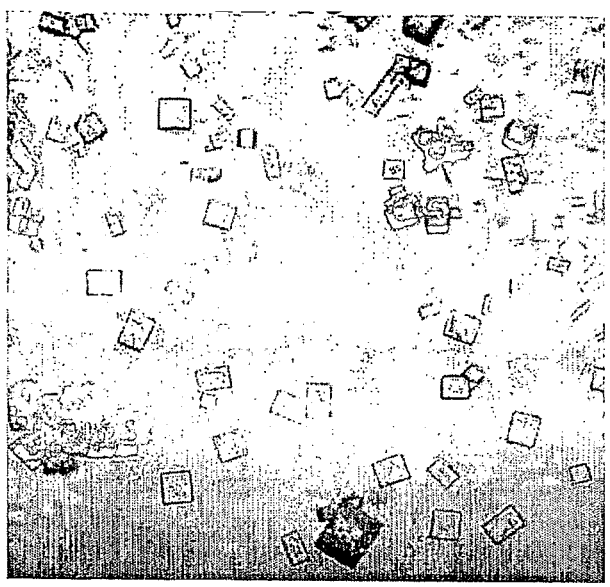
FIG. 12 presents images of creatine kinase 1 crystals (A), beta-human growth factor crystals (B) and an avidin crystal (C).
Figure 12:
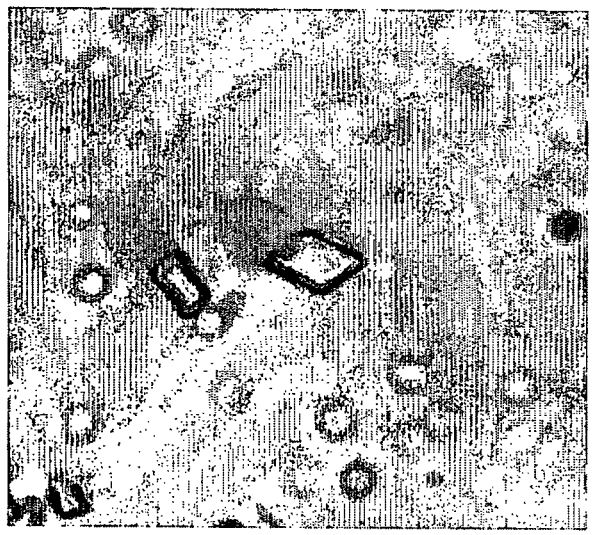
Figure 12:
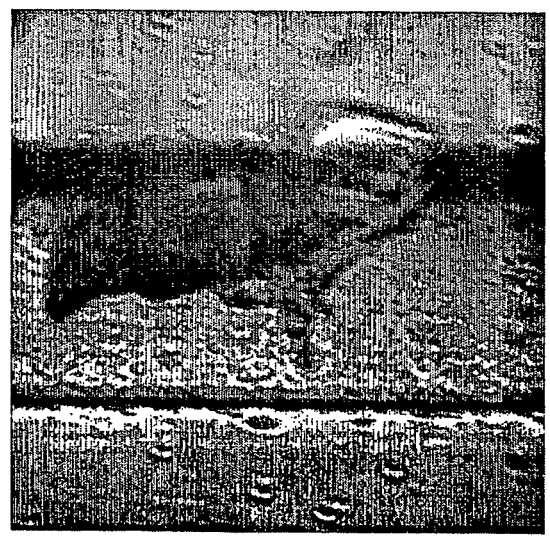
Figure 13:
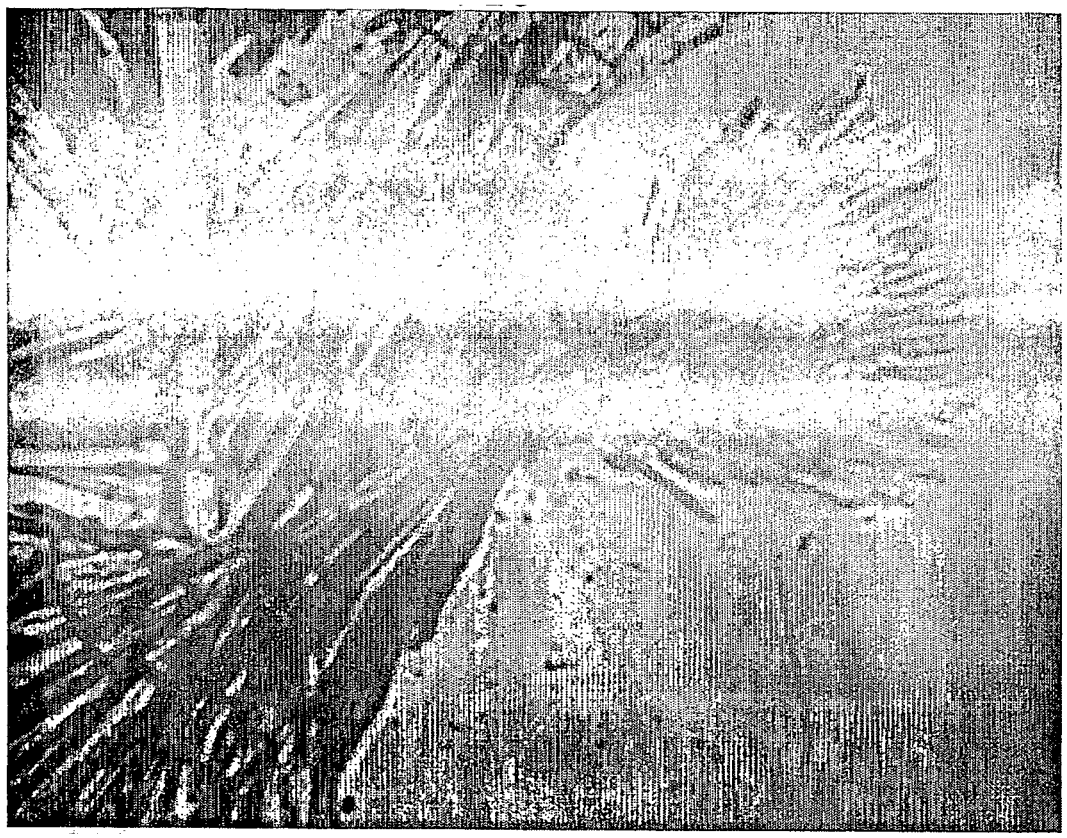
FIG. 13 presents protein crystals of herceptin (A) and Ly1 lysozyme (B).
Figure 13:
Figure 14:
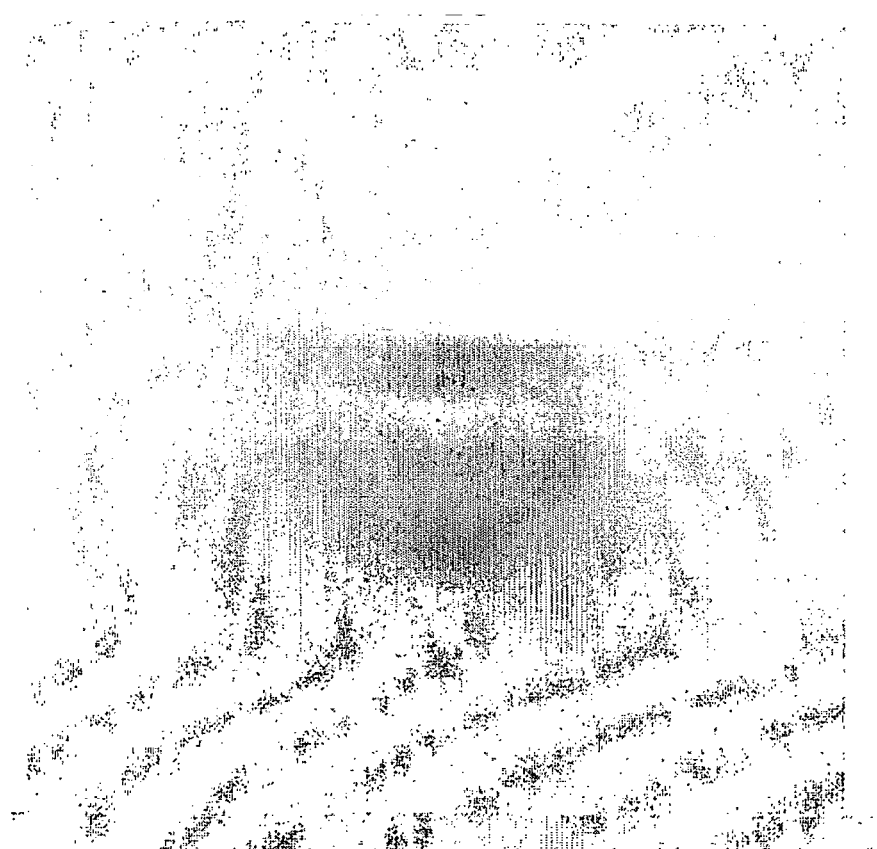
FIG. 14 exhibits diffraction patterns of a Lysozyme crystal (A) and a ribonuclease-1 crystal (B).
Figure 14:
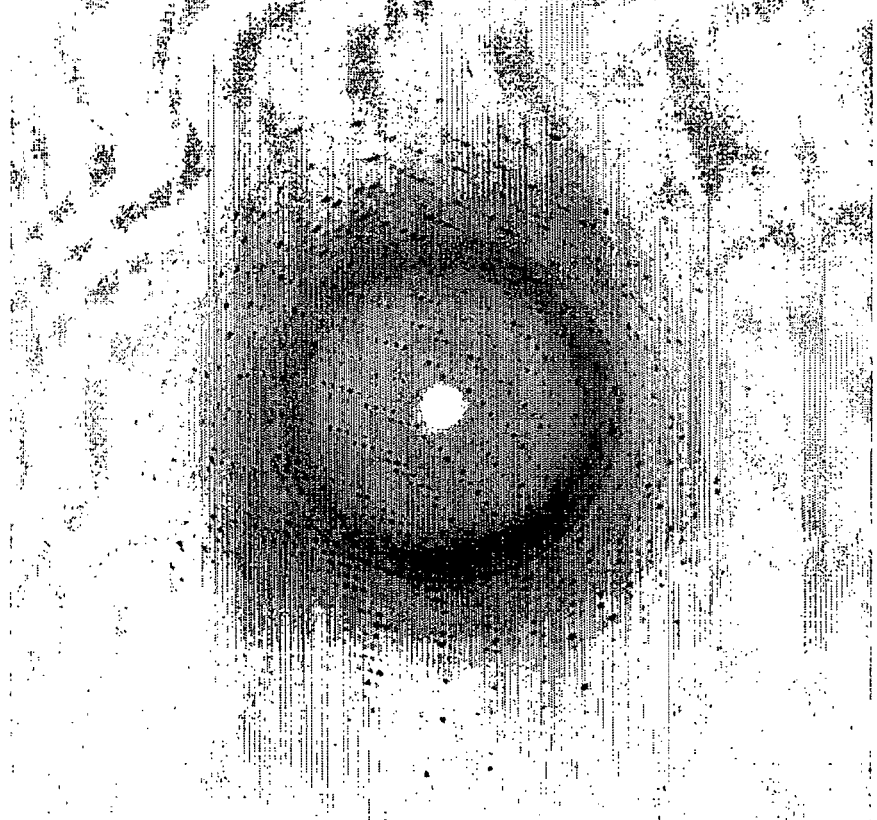
Figure 15:
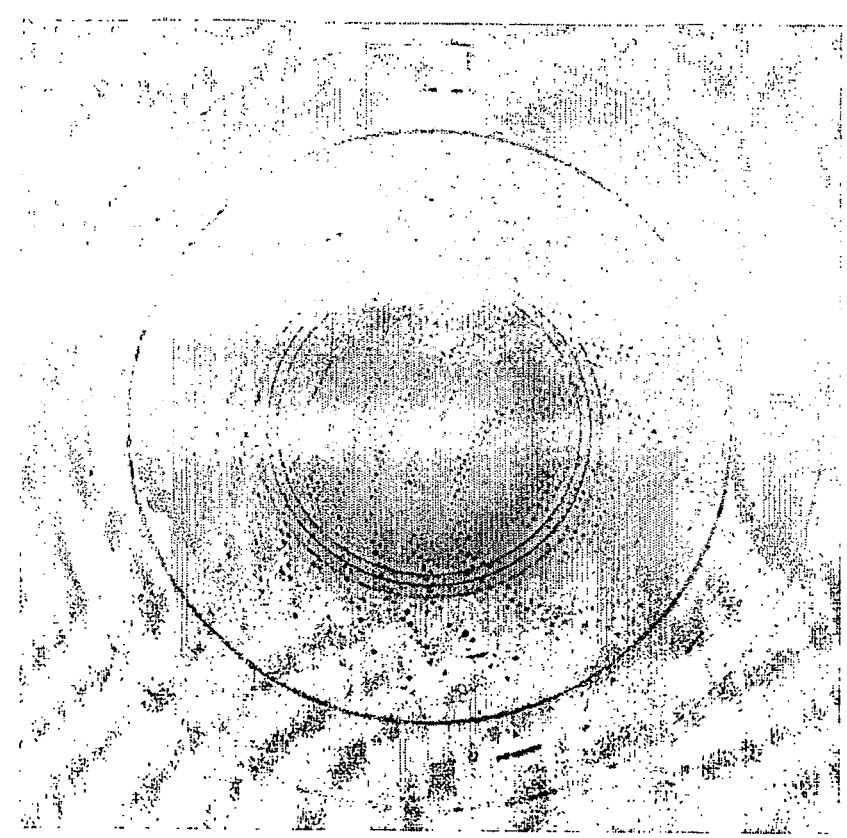
FIG. 15 shows the diffraction patterns of a prostaglandin crystal (A) and of a crystallization reactor consisting of a polymerized IEF buffer devoid of protein crystals (B).
Figure 15:
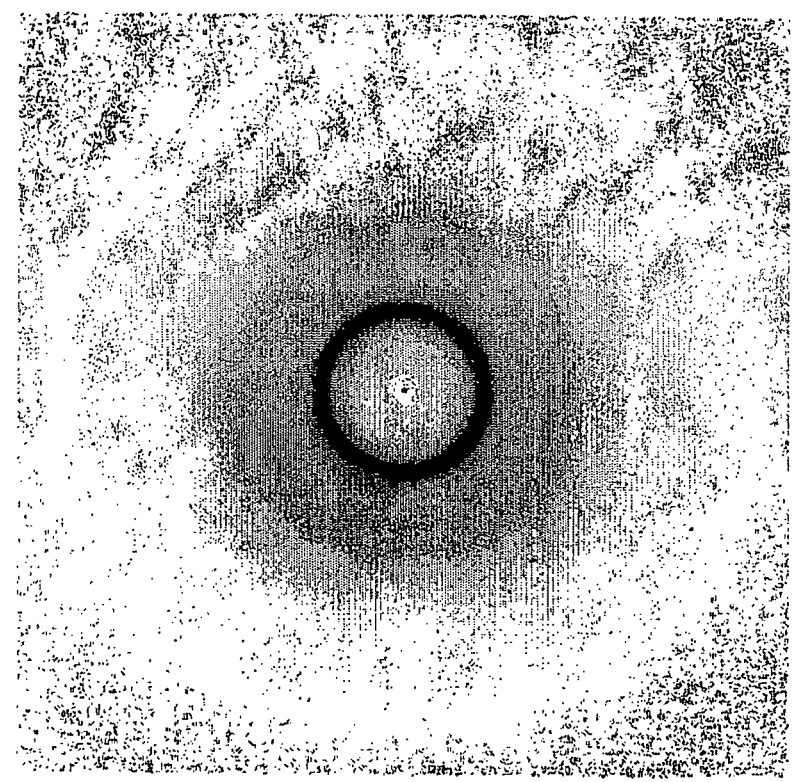

A solution of Bovine Carbonic Anhydrase (1 μg/ml; Sigma), having a pI of 5.95, was concentrated by IEF into a pH gel compartment (cavities; 4% polyacrylamide) with a pH of 5.8-6.0. The concentration procedure took 40 minutes at 25° C. and under an electric field of 100 V/cm. After 40 min. a crystal was obtained (FIG. 10).

Example 8

Crystallization of Pepsin 4 Creatine Kinase 1, Beta-human Growth Factor, Avidin, Herceptin, Ly1 Lysozyme, Ribonuclease-1 and Prostaglandin Protein crystallization of pepsin-4, creatine kinase (CK), beta-human growth factor (βhGF), avidin, herceptin, Ly1 lysozyme, ribonuclease-1 (RNAse-1) and prostaglandin was performed as detailed in Table 1. The resulting crystals and/or diffraction fraction of the crystallized protein are represented in FIGS. 11-15.

TABLE 1

| Protein | pI | Content of reactor | Electric field (V/cm) | Crystal formation time (h) |
| --- | --- | --- | --- | --- |
| Pepsin | 1.0 | 4% PAAG[1] Water | 1000 | 2 |
| CK | 6.57 | 6% PAAG Glutamic acid-Tris (1 mM) | 1000 | 3 |
| β-hGF | 4.5 | 4% PAAG Glutamic acid-HEPES (1 mM) | 1000 | 2 |
| avidin | 10.0 | 6% PAAG 0.1%% carrier ampholytes (pH 8-11) | 500 | 4 |
| Herceptin | 9.4 | 4% PAAG 0.1%% carrier ampholytes (pH 8-11) | 500 | 4 |
| Ly1 | 10.7 | 6% PAAG 0.1%% carrier ampholytes (pH 8-11) | 1000 | 2 |
| RNAse-1 | 7.8 | 4% PAAG Glutamic acid-HEPES (1 mM) | 500 | 7 |
| prostaglandin | 4.6 | 6% PAAG Glutamic acid-HEPES (1 mM) | 1000 | 10 |

[1]polyacrylamide gel

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for rapid crystallization of biomolecules, comprising:
   (a) providing at least one biomolecules species;
   (b) providing at least one crystallization reactor comprising an isoelectric focusing buffer having a pH range, the pH range encompassing the pI of the at least one biomolecule species;

(c) bringing said at least one biomolecule species into contact with the at least one crystallization reactor;
(d) introducing an electric field at said at least one crystallization reactor thereby generating a concentrated solution of said at least one biomolecule species; and
(e) obtaining at least one crystal within said at least one crystallization reactor;
wherein the electric field is within the range of 50-2,000 V/cm.

2. The method according to claim 1, wherein step (c) further comprises depositing the at least one crystallization reactor and the at least one biomolecule species in running buffer.

3. The method according to claim 1, wherein step (e) further comprises extracting a biomolecule crystal from said at least one crystallization reactor.

4. The method according to claim 1, wherein the crystallization occurs within less than 12 hours.

5. The method according to claim 1, wherein the at least one biomolecule species is selected from the group consisting of peptides, proteins, glycoproteins, polypeptides, enzymes, antibodies, protein-DNA complexes, protein complexes comprising chemical entities, polynucleotides, DNA, RNA, antigens, antigenic epitopes and variants thereof, hormones, carbohydrates, lipids, phospholipids and biotinylated probes.

6. The method according to claim 5, wherein the biomolecule species is a protein.

7. The method according to claim 6, wherein the protein is recombinant.

8. A method for rapid crystallization of biomolecules, comprising:
(a) providing at least one biomolecules species;
b) providing at least one crystallization reactor comprising an isoelectric focusing buffer having a pH range, the pH range encompassing the pI of the at least one biomolecule species;
(c) bringing said at least one biomolecule species into contact with the at least one crystallization reactor;
(d) introducing an electric field at said at least one crystallization reactor thereby generating a concentrated solution of said at least one biomolecule species; and
(e) obtaining at least one crystal within said at least one crystallization reactor;
wherein the at least one biomolecule species in step (a) is immobilized onto a substrate comprising a porous web material.

9. The method according to claim 1, wherein the at least one crystallization reactor is provided within a capillary.

10. A method for rapid crystallization of biomolecules, comprising:
(a) providing at least one biomolecules species;
(b) providing at least one crystallization reactor comprising an isoelectric focusing buffer having a pH range, the pH range encompassing the pI of the at least one biomolecule species;
(c) bringing said at least one biomolecule species into contact with the at least one crystallization reactor;
(d) introducing an electric field at said at least one crystallization reactor thereby generating a concentrated solution of said at least one biomolecule species; and
(e) obtaining at least one crystal within said at least one crystallization reactor;
wherein the at least one crystallization reaction is linked, joined, or substantially contiguous to a solid substrate comprising a porous web material.

11. The method according to claim 1, wherein the isoelectric focusing buffer further comprises a polymer.

12. The method according to claim 11, wherein the polymer is selected from the group consisting of: linear polymers, branched polymers, polyacrylamide, agarose, hydrogels, cellulose, modified cellulose, cross-linked polyvinyl alcohol, cross-linked polyethylene oxide and glycol polymer.

13. The method according to claim 1, wherein the isoelectric focusing buffer has a pH range of no more than 0.2 pH units.

14. The method according to claim 1, wherein in step (b) a plurality of crystallization reactors is provided, each crystallization reactor comprising an isoelectric focusing buffer.

15. The method according to claim 14, wherein a distinct protein species is crystallized in each crystallization reactor and wherein each distinct protein species has a distinct isoelectric point.

16. The method according to claim 14, wherein the isoelectric focusing buffers in the plurality of crystallization reactors are different from one another.

17. The method according to claim 14, wherein the crystallization reactors are isolated from one another.

18. The method according to claim 14, wherein the plurality of crystallization reactors are linked, joined, or substantially contiguous to a substrate.

19. The method according to claim 1, wherein the crystallization reactor is selected from the group consisting of: immobilized pH gradient strips, pH membranes and pre-cast gels.

20. The method according to claim 1, further comprising prior to step (a) the step of sorting a solution comprising at least one biomolecule species.

21. A method for sorting a solution comprising a plurality of biomolecules and rapidly crystallizing at least one biomolecule species, comprising:
(a) providing a medium comprising a plurality of biomolecules;
(b) sorting the plurality of biomolecules on a substrate, thereby obtaining at least one locus on the substrate comprising at least one biomolecule species;
(c) recovering a portion from said substrate, the portion comprising the at least one locus;
(d) providing at least one crystallization reactor comprising an isoelectric focusing buffer having a pH range, the pH range encompassing the pI of the at least biomolecule:
(e) bringing the portion of (c) into contact with the at least one crystallization reactor;
(f) introducing an electric field at the at least one crystallization reactor thereby generating within said at least one crystallization reactor a concentrated solution of said at least one biomolecule species; and
(g) obtaining at least one crystal within said at least one crystallization reactor of (f).

22. The method according to claim 21, wherein step (b) is carried out by a method selected from the group consisting of: isoelectric focusing, thin layer chromatography, including High Performance Liquid Chromatography (HPLC) techniques, and gel electrophoresis.

23. The method according to claim 22, wherein the method is performed under non-denaturing conditions.

24. The method according to claim 21, wherein sorting in step (b) is by the mass of the at least one biomolecule species.

25. The method according to claim 21, wherein step (e) further comprises depositing said portion and the at least one crystallization reactor in running buffer.

26. The method according to claim 21, wherein the at least one biomolecule species is a protein.

27. The method according to claim 21, wherein the electric field is within the range of 50-2,000 V/cm and the crystals are obtained within less than 12 hours.

28. The method according to claim 21, wherein the isoelectric focusing buffer comprises a polymer selected from the group consisting of: polyacrylamide, agarose, hydrogels, cellulose, nitrocellulose, modified cellulose, cross-linked polyvinyl alcohol, cross-linked polyethylene oxide and glycol polymer.

29. The method according to claim 21, wherein the substrate in step (b) is a gel.

30. The method according to claim 21, wherein in step (d) a plurality of crystallization reactors comprising a plurality of isoelectric focusing buffers is provided, each isoelectric focusing buffer establishing a pH range, wherein at least one isoelectric focusing buffer establishes a pH range encompassing the pI of the at least one biomolecule.

31. The method according to claim 30, wherein each isoelectric focusing buffer comprises a polymer.

32. The method according to claim 30, wherein the plurality of crystallization reactors are isolated from one another.

33. The method according to claim 30, wherein the plurality of crystallization reactors are linked, joined, or substantially contiguous to a substrate comprising a porous web material.

34. The method according to claim 21, wherein the crystallization reactor is selected from the group consisting of: immobilized pH gradient strips, pH membranes and pre-cast gels.

35. An apparatus suitable for inducing rapid formation of biomolecule crystals, comprising:
 (a) a buffer chamber having an upper side and a lower side, the lower side being sealed with a bottom such that the buffer chamber encloses at least one buffer compartment capable of holding fluids;
 (b) at least one crystallization reactor contained within said buffer chamber, the at least one crystallization reactor comprising an isoelectric focusing buffer;
 (c) a device for generating an electrical field;
 (d) two salt bridges having two ends, one end of each salt bridge being in contact with one end of the holder and one end of each salt bridge being contained within the at least one buffer chamber; and, optionally,
 (e) means for circulating fluids contained within the at least one buffer compartment.

36. The apparatus according to claim 35, wherein component (b) is a holder having two ends, an upper side and a lower side, the holder encompasses at least one crystallization reactor, the at least one crystallization reactor comprising an isoelectric focusing buffer, wherein the holder is contained within the buffer compartment.

37. The apparatus according to claim 35, comprising two buffer chambers, each buffer chamber enclosing one end of one salt bridge.

38. The apparatus according to claim 35, further comprising a temperature-controlled module enabling to manage the temperature at the at least one crystallization reactor.

39. The apparatus according to claim 35, wherein component (b) comprises a holder adapted for supporting a substrate and comprising at least one crystallization reactor.

40. The apparatus according to claim 39, wherein the holder is a capillary adapted for comprising at least one crystallization reactor.

41. The apparatus according to claim 39, wherein the holder encompasses at least one cavity wherein the at least one cavity is adapted for containing a crystallization reactor.

42. The apparatus according to claim 41, wherein the crystallization reactor is selected from the group consisting of: immobilized pH gradient strips, ph membranes and pre-cast gels.

43. The apparatus according to claim 35, wherein the buffer chamber comprises a non-conductive material.

44. The apparatus to claim 39, wherein the holder comprises a material having a larger resistance than that of the polymer comprised within the crystallization reactor.

45. The apparatus according to claim 43, wherein the non-conductive material is selected from the group consisting of: ply-N-methyl methacrylamide, acrylic, lucite, polystyrene, ceramic, glass and poly-methyl-methacrylate.

46. The apparatus according to claim 39, wherein the holder comprises a material that is impermeable to biomolecules.

47. The apparatus according to claim 35, wherein the device for generating an electrical field comprises a plurality of electrodes.

48. The apparatus according to claim 47, wherein the plurality of electrodes comprises a metal selected from the group consisting of: platinum, titanium, chromium, gold, tantalum, palladium, palladium oxide, germanium, nickel and rhodium or alloys comprising same.

49. The apparatus according to claim 35, wherein the device for generating an electrical field supplies DC or AC currents and generates an electric field within the range of 50-2,000 V/cm.

50. The apparatus according to claim 35, wherein the buffer compartment is adapted for holding a solution comprising running buffer and at least one biomolecule dissolved with the running buffer.

51. The apparatus according to claim 35, further being automated.

52. The apparatus according to claim 35, wherein the biomolecule is selected from the group consisting of: peptides, proteins, glycoproteins, polypeptides, enzymes, antibodies, protein-DNA complexes, protein complexes comprising chemical entities, polynucleotides, DNA, RNA, antigens, antigenic epitopes and variants thereof, hormones, carbohydrates, lipids, phospholipids and biotinylated probes.

53. The apparatus according to claim 52, wherein the biomolecule is a protein.

54. The apparatus according to claim 35, wherein crystallization occurs within less than 12 hours.

55. The apparatus according to claim 47, comprising two buffer chambers, each buffer chamber enclosing one electrode.

* * * * *